US006107026A

United States Patent [19]

Lange, III et al.

[11] Patent Number: 6,107,026

[45] Date of Patent: Aug. 22, 2000

[54] METHODS AND REAGENTS FOR RFLP ANALYSIS OF THE HUMAN PANCREATIC CHOLESTEROL ESTERASE GENE

[76] Inventors: Louis G. Lange, III, 38 Kingsbury Pl., St. Louis, Mo. 63112; Buddhiraja Vijaya Kumar, 2725 Creekmont La., St. Louis, Mo. 63125

[21] Appl. No.: 08/370,223

[22] Filed: Jan. 9, 2000

Related U.S. Application Data

[63] Continuation of application No. 08/053,308, Apr. 26, 1993, abandoned, which is a continuation of application No. 07/730,204, Jul. 15, 1991, abandoned.

[51] Int. Cl.$^{7}$ .............................. C12Q 1/68; C12P 19/34; C07H 21/04; C12N 15/00

[52] U.S. Cl. ............................ 435/6; 435/91.1; 435/91.2; 536/23.5; 536/24.31; 536/25.4; 536/25.32

[58] Field of Search ............................ 435/6, 91.1, 91.2; 536/23.5, 24.31, 25.4, 25.32; 935/76, 77

[56] References Cited

PUBLICATIONS

Sommer et al., "Minimal homology requirements for PCR primers", *Nucleic Acids Research*, vol. 17, No. 16, 1989, p. 6749.
Botstein et al., Am. J. Hum. Genet. 32:314–331 (1980).
Norum et al., Physiol. Rev. 63:1343–1419 (1983).
Katathanasis et al., Nature 304:371–373 (1983).
Karathanasis et al., Nature 305:823–825 (1983).
Lehrman et al., Proc. Natl. Acad. Sci USA 83:3679–3683 (1986).
Bosner et al., Proc. Natl. Acad. Sci USA 85:7438–7442 (1988).
Hobbs et al., J. Clin. Invest. 81:909–917 (1988).
Cooper & Clayton, Hum. Genet. 78:299–312 (1988).
Ordovas & Schaefer, Ann. Biol. Clin. (Paris) 46:24–29 (1988).
Kyger et al., Biochem. Biophys. Res. Comm. 164:1302–1309.
Kissel et al., Biochim Biophys. Acta 1006:227–236 (1989).
Nilsson et al., Eur. J. Biochem. 192:543–550 (1990).
Daga et al., Hum. Genet. 84:412–416 (1990).
Johansen et al., Clin. Genet. 37:194–197 (1990).
Berg, Acta Genet. Med. Gemellol. (Roma) 39:15–24 (1990).
Taylor et al., Genomics 10:425–431 (1991).
Funke et al., J. Clin. Invest. 87:371–376 (1991).
Huang and Hiu, J. Lipid Res. 31:2029–2037 (1991).
Antonakis, N.E.J.M. 320:153–163 (1989).
Shaw et al., Hum. Genet. 74:267–269 (1986).

*Primary Examiner*—W. Gary Jones
*Assistant Examiner*—Bradley L. Sisson
*Attorney, Agent, or Firm*—Banner & Allegretti, Ltd.

[57] ABSTRACT

This invention relates to the identification of restriction fragment length polymorphisms (RFLP) of the human pancreatic cholesterol esterase gene. Specifically, the invention relates to the use of RFLP analysis for identifying individuals with a particular genetic variant of the human pancreatic cholesterol esterase gene. The invention also relates to treatment of individuals with therapeutic drugs for the prevention or alleviation of disease states in a human related to cholesterol metabolism.

11 Claims, 15 Drawing Sheets

SHEET 1

*FIG. 2A*

```
GAATTCCGGA  TCAATACAGT  TTACCTTCTG  TATCAGTTAA  GTGTCAAGAT  GGAAGGAACA      60

GCAGTCTCAA  GATAATGCAA  AGAGTTTATT  CATCCAGAGG  CTG ATG CTC ACC ATG         115
                                                    Met Leu Thr Met
                                                      1

GGG CGC CTG CAA CTG GTT GTG TTG GGC CTC ACC TGC TGC TGG GCA GTG              163
Gly Arg Leu Gln Leu Val Val Leu Gly Leu Thr Cys Cys Trp Ala Val
  5                  10                  15                  20

GCG AGT GCC GCG AAG CTG GGC GCC GTG TAC ACA GAA GGT GGG TTC GTG              211
Ala Ser Ala Ala Lys Leu Gly Ala Val Tyr Thr Glu Gly Gly Phe Val
                 25                  30                  35

GAA GGC GTC AAT AAG AAG CTC GGC CTC CTG GGT GAC TCT GTG GAC ATC              259
Glu Gly Val Asn Lys Lys Leu Gly Leu Leu Gly Asp Ser Val Asp Ile
             40                  45                  50

TTC AAG GGC ATC CCC TTC GCA GCT CCC ACC AAG GCC CTG GAA AAT CCT              307
Phe Lys Gly Ile Pro Phe Ala Ala Pro Thr Lys Ala Leu Glu Asn Pro
         55                  60                  65

CAG CCA CAT CCT GGC TGG CAA GGG ACC CTG AAG GCC AAG AAC TTC AAG              355
Gln Pro His Pro Gly Trp Gln Gly Thr Leu Lys Ala Lys Asn Phe Lys
     70                  75                  80

AAG AGA TGC CTG CAG GCC ACC ATC ACC CAG GAC AGC ACC TAC GGG GAT              403
Lys Arg Cys Leu Gln Ala Thr Ile Thr Gln Asp Ser Thr Tyr Gly Asp
 85                  90                  95                 100
```

*FIG. 2B*

```
GAA GAC TGC CTG TAC CTC AAC ATT TGG GTG CCC CAG GGC AGG AAG CAA   451
Glu Asp Cys Leu Tyr Leu Asn Ile Trp Val Pro Gln Gly Arg Lys Gln
                105                 110                 115

GTC TCC CGG GAC CTG CCC GTT ATG ATC TGG ATC TAT GGA GGC GCC TTC   499
Val Ser Arg Asp Leu Pro Val Met Ile Trp Ile Tyr Gly Gly Ala Phe
            120                 125                 130

CTC ATG GGG TCC GGC CAT GGG GCC AAC TTC CTC AAC AAC TAC CTG TAT   547
Leu Met Gly Ser Gly His Gly Ala Asn Phe Leu Asn Asn Tyr Leu Tyr
        135                 140                 145

GAC GGC GCG GCG ATC GCC ACA CGC GGA AAC GTC ATC GTG GTC ACC TTC   595
Asp Gly Glu Glu Ile Ala Thr Arg Gly Asn Val Ile Val Val Thr Phe
    150                 155                 160

AAC TAC CGT GTC GGC CCC CTT GGG TTC CTC AGC ACT GGG GAC GCC AAT   643
Asn Tyr Arg Val Gly Pro Leu Gly Phe Leu Ser Thr Gly Asp Ala Asn
165                 170                 175                 180

CTG CCA GGT AAC TAT GGC CTT CGG GAT CAG CAC ATG GCC ATT GCT TGG   691
Leu Pro Gly Asn Tyr Gly Leu Arg Asp Gln His Met Ala Ile Ala Trp
                185                 190                 195

GTG AAG AGG AAT ATC GCG GCC TTC GGG GGG GAC CCC AAC AAC ATC ACG   739
Val Lys Arg Asn Ile Ala Ala Phe Gly Gly Asp Pro Asn Asn Ile Thr
            200                 205                 210
```

*FIG. 2C*

```
CTC TTC GGG GAG TCT GCT GGA GGT GCC AGC GTC TCT CTG CAG ACC CTC     787
Leu Phe Gly Glu Ser Ala Gly Gly Ala Ser Val Ser Leu Gln Thr Leu
        215                 220                 225

TCC CCC TAC AAC AAG GGC CTC ATC CGG CGA GCC ATC AGC CAG AGC GGC     835
Ser Pro Tyr Asn Lys Gly Leu Ile Arg Arg Ala Ile Ser Gln Ser Gly
    230                 235                 240

GTG GCC CTG AGT CCC TGG GTC ATC CAG AAA AAC CCA CTC TTC TGG GCC     883
Val Ala Leu Ser Pro Trp Val Ile Gln Lys Asn Pro Leu Phe Trp Ala
245                 250                 255                 260

AAA AAG GTG GCT GAG AAG GTG GGT TGC CCT GTG GGT GAT GCC GCC AGG     931
Lys Lys Val Ala Glu Lys Val Gly Cys Pro Val Gly Asp Ala Ala Arg
                265                 270                 275

ATG GCC CAG TGT CTG AAG GTT ACT GAT CCC CGA GCC CTG ACG CTG GCC     979
Met Ala Gln Cys Leu Lys Val Thr Asp Pro Arg Ala Leu Thr Leu Ala
            280                 285                 290

TAT AAG GTG CCG CTG GCA GGC CTG GAG TAC CCC ATG CTG CAC TAT GTG    1027
Tyr Lys Val Pro Leu Ala Gly Leu Glu Tyr Pro Met Leu His Tyr Val
        295                 300                 305

GGC TTC GTC CCT GTC ATT GAT GGA GAC TTC ATC CCC GCT GAC CCG ATC    1075
Gly Phe Val Pro Val Ile Asp Gly Asp Phe Ile Pro Ala Asp Pro Ile
    310                 315                 320
```

*FIG. 2D*

```
AAC CTG TAC GCC AAC GCC GCC GAC ATC GAC TAT ATA GCA GGC ACC ACC    1123
Asn Leu Tyr Ala Asn Ala Ala Asp Ile Asp Tyr Ile Ala Gly Thr Asn
325                 330                 335                 340

AAC ATG GAC GGC CAC ATC TTC GCC AGC ATC GAC ATG CCT GCC ATC AAC    1171
Asn Met Asp Gly His Ile Phe Ala Ser Ile Asp Met Pro Ala Ile Asn
                345                 350                 355

AAG GGC AAC AAG AAA GTC ACG GAG GAG GAC TTC TAC AAG CTG GTC AGT    1219
Lys Gly Asn Lys Lys Val Thr Glu Glu Asp Phe Tyr Lys Leu Val Ser
            360                 365                 370

GAG TTC ACA ATC ACC AAG GGG CTC AGA GGC GCC AAG ACG ACC TTT GAT    1267
Glu Phe Thr Ile Thr Lys Gly Leu Arg Gly Ala Lys Thr Thr Phe Asp
        375                 380                 385

GTC TAC ACC GAG TCC TGG GCC CAG GAC CCA TCC CAG GAG AAT AAG AAG    1315
Val Tyr Thr Glu Ser Trp Ala Gln Asp Pro Ser Gln Glu Asn Lys Lys
    390                 395                 400

AAG ACT GTG GTG GAC TTT GAG ACC GAT GTC CTC TTC CTG GTG CCC ACC    1363
Lys Thr Val Val Asp Phe Glu Thr Asp Val Leu Phe Leu Val Pro Thr
405                 410                 415                 420

GAG ATT GCC CTA GCC CAG CAC AGA GCC AAT GCC AAG AGT GCC AAG ACC    1411
Glu Ile Ala Leu Ala Gln His Arg Ala Asn Ala Lys Ser Ala Lys Thr
                425                 430                 435
```

FIG. 2E

```
TAC GCC TAC CTG TTT TCC CAT CCC TCT CGG ATG CCC GTC TAC CCC AAA     1459
Tyr Ala Tyr Leu Phe Ser His Pro Ser Arg Met Pro Val Tyr Pro Lys
            440                 445                 450

TGG GTG GGG GCC GAC CAT GCA GAT GAC ATT CAG TAC GTT TTC GGG AGG     1507
Trp Val Gly Ala Asp His Ala Asp Asp Ile Gln Tyr Val Phe Gly Lys
        455                 460                 465

CCC TTC GCC ACC CCC ACG GGC TAC CGG CCC CAA GAC AGG ACA GTC TCT     1555
Pro Phe Ala Thr Pro Thr Gly Tyr Arg Pro Gln Asp Arg Thr Val Ser
    470                 475                 480

AAG GCC ATG ATC GCC TAC TGG ACC AAC TTT GCC AAA ACA GGG GAC CCC     1603
Lys Ala Met Ile Ala Tyr Trp Thr Asn Phe Ala Lys Thr Gly Asp Pro
485                     490                 495                 500

ACC ATG GGC GAC TCG GCT GTG CCC ACA CAC TGG GAA CCC TAC ACT ACG     1651
Asn Met Gly Asp Ser Ala Val Pro Thr His Trp Glu Pro Tyr Thr Thr
                505                     510                 515

GAA AAC AGC GGC TAC CTG GCG ATC ACC AAG AAG ATG GGC AGC AGC TCC     1699
Glu Asn Ser Gly Tyr Leu Glu Ile Thr Lys Lys Met Gly Ser Ser Ser
            520                     525                 530

ATG AAG CGG AGC CTG AGA ACC AAC TTC CTG CGC TAC TGG ACC CTC ACC     1747
Met Lys Arg Ser Leu Arg Thr Asn Phe Leu Arg Tyr Trp Thr Leu Thr
        535                     540                 545
```

*FIG. 2F*

```
TAT CTG GCG CTG CCC ACA GTG ACC GAC CAG GCG GCC ACC CCT GTG CCC     1795
Tyr Leu Ala Leu Pro Thr Val Thr Asp Gln Glu Ala Thr Pro Val Pro
    550                     555                 560

CCC ACA GGG GAC TCC GAG GCC ACT CCC GTG CCC CCC ACG GGT GAC TCC     1843
Pro Thr Gly Asp Ser Glu Ala Thr Pro Val Pro Pro Thr Gly Asp Ser
565                 570                 575                 580

GAG ACC GCC CCC GTG CCG CCC ACG GGT GAC TCC GGG GCC CCC CCC GTG     1891
Glu Thr Ala Pro Val Pro Pro Thr Gly Asp Ser Gly Ala Pro Pro Val
                585                 590                 595

CCG CCC ACG GGT GAC TCC GGG GCC CCC CCC GTG CCG CCC ACG GGT GAC     1939
Pro Pro Thr Gly Asp Ser Gly Ala Pro Pro Val Pro Pro Thr Gly Asp
            600                 605                 610

TCC GGG GCC CCC CCC GTG CCG CCC ACG GGT GAC TCC GGG GCC CCC CCC     1987
Ser Gly Ala Pro Pro Val Pro Pro Thr Gly Asp Ser Gly Ala Pro Pro
        615                 620                 625

GTG CCG CCC ACG GGT GAC TCC GGG GCC CCC CCC GTG CCG CCC ACG GGT     2035
Val Pro Pro Thr Gly Asp Ser Gly Ala Pro Pro Val Pro Pro Thr Gly
    630                 635                 640

GAC TCC GGG GCC CCC CCC GTG CCG CCC ACG GGT GAC TCC GGC GCC CCC     2083
Asp Ser Gly Ala Pro Pro Val Pro Pro Thr Gly Asp Ser Gly Ala Pro
645                 650                 655                 660
```

*FIG. 2G*

```
CCC GTG CCG CCC ACG GGT GAC GCC GGG CCC CCC CCC GTG CCG CCC ACG   2131
Pro Val Pro Pro Thr Gly Asp Ala Gly Pro Pro Pro Val Pro Pro Thr
                665                 670                 675

GGT GAC TCC GGC GCC CCC CCC GTG CCG CCC ACG GGT GAC TCC GGG GCC   2179
Gly Asp Ser Gly Ala Pro Pro Val Pro Pro Thr Gly Asp Ser Gly Ala
            680                 685                 690

CCC CCC GTG ACC CCC ACG GGT GAC TCC GCG ACC GCC CCC GTG CCG CCC   2227
Pro Pro Val Thr Pro Thr Gly Asp Ser Glu Thr Ala Pro Val Pro Pro
        695                 700                 705

ACG GGT GAC TCC GGG GCC CCC CCT GTG CCC CCC ACG GGT GAC TCT GAG   2275
Thr Gly Asp Ser Gly Ala Pro Pro Val Pro Pro Thr Gly Asp Ser Glu
    710                 715                 720

GCT GCC CCT GTG CCC CCC ACA GAT GAC TCC AAG GAA GCT CAG ATG CCT   2323
Ala Ala Pro Val Pro Pro Thr Asp Asp Ser Lys Glu Ala Gln Met Pro
725                     730                 735                 740

GCA GTC ATT AGG TTT TAGCGTCCCA TGAGCCTTGG TATCAAGAGG CCACAAGAGT   2378
Ala Val Ile Arg Phe
                745

GGGACCCCAG GGGCTCCCCT CCCATCTTGA GCTCTTCCTG AATAAAGCCT CATACCCCTG 2438

GGGCCCAACT GTACCCATCA CCTGGTACAA AAAAAAAAAA AAAGAATTC            2487
```

*FIG. 3A*

```
GAATTCCGGA  TCAATACAGT  TTACCTTCTG  TATCAGTTAA  GTGTCAAGAT  GGAAGGAACA   60
GCAGTCTCAA  GATAATGCAA  AGAGTTTATT  CATCCAgt--  tgatcaagcg  gtcaaacatg  118
acgacattcg  cgcccagaca  ataagagtac  agacgtgcaa  gcgtaagtga  gggaagtgcc  178
taggctcgcg  atgagagtaa  gtagcctcgg  aggcccaggg  ggagggggat  cccctagGAG  238
GCTGATGCTC  ACCATGGGGC  GCCTGCAACT  GGTTGTGTTG  GGCCTCACCT  GCTGCTGGGCA 298
GTGGCGAGTG  CCGCGAAGgt  aagagcccag  cggaggggca  ggtcctgctg  ctctctcgct  358
caatcagatc  tggaaacttc  gggccaggct  gagaaagagc  ccagcacagc  cccgcagcag  418
atcccgggca  ctaccgtcat  ttctatggga  caggtgccag  gtagaacacg  gatgccaatt  478
ccatttgaat  ttcagataac  ---aacccaa  cctccatccc  acctcttggc  cggcttccct  535
agtgggaaca  ctggttaacc  agttttcctc  taagattctg  gagcagacac  cccagggata  595
agagaggaac  aggaatccta  aagccctgag  cattgcaggg  caggggtgc   tgcctgggtc  655
tcctgtgcag  agctgtcctg  ctttgaagct  gtctttgcct  ctgggcacga  ggagtcggct  715
tccttgcccc  tgggattcag  gccgatggct  tgagcccccct gaccctgccc  gtgtctccct  775
cgcagCTGGG  CGCCGTGTAC  ACAGAAGGTG  GGTTCGTGGA  AGGCGTCAAT  AAGAAGCTCG  835
GCCTCCTGGG  TGACTCTGTG  GACATCTTCA  AGGGCATCCC  CTTCGCAGCT  CCCACCAAGG  895
```

*FIG. 3B*

```
CCCTGGAAAA  TCCTCAGCCA  CATCCTGGCT  GGCAAGgtgg  gtggtgtccg  ccactcccct   955
ccggggggta  aggccccggt  tccttcctca  tgccaactcc  ggtccaccgt  caggacccta  1015
aggcaagaac  ttcaagagaa  tctccagcac  catacc----  agtgggtggt  gaggactggc  1071
tggggggggg  ggggtgaggg  ggctgccttcc ctcatgccaa  ctcctgccac  ctgcagGGAC  1131
CCTGAAGGCC  AAGAACTTCA  AGAAGAGATG  CCTGCAGGCC  ACCATCACCC  AGGACAGCAC  1191
CTACGGGGAT  GAAGACTGCC  TGTACCTCAA  CATTTGGGTG  CCCCAGGGCA  GGAAGCAAGg  1251
tctgcctccc  ctctactccc  aaggaccctc  ccatgcagcc  cactgccccg  ggtctactcc  1311
tggcttgagt  ctgggggctg  caaagctgaa  cttccatgaa  atcccacaga  ggcggggagg  1371
ggagcgccca  ctgccgttgc  ccagcctggg  gcagggcagc  gccttggagc  acctccctgt  1431
cttggcccca  ggcacctgct  gcacagggac  agggaccggc  tggagacagg  gccaggcggg  1491
gcgtctgggg  tcaccagccg  ctcccccatc  tcagTCTCCC  GGGACCTGCC  CGTTATGATC  1551
TGGATCTATG  GAGGCGCCTT  CCTCATGGGG  TCCGGCCATG  GGGCCAACTT  CCTCAACAAC  1611
TACCTGTATG  ACGGCGAGGC  GATCGCCACA  CGCGGAAACG  TCATCGTGGT  CACCTTCAAC  1671
TACCGTGTCG  GCCCCCTTGG  GTTCCTCAGC  ACTGGGGACG  CCATCTGCC   Aggtcctgag  1731
gtgggccgaa  accagcatga  gggagcaggg  agatttcat-  ---aaatgag  aagagatggg  1787
```

*FIG. 3C*

| | | | | | | |
|---|---|---|---|---|---|---|
| tagggagaca | gtgatggctg | acatctaaaa | cacccctag | acacaccaac | ccaacctcct | 1847 |
| ggaacccacc | catacagcac | cgaacccagc | tcagcctagt | ctcctgggac | ccaccccctc | 1907 |
| cagcacccta | cccgacccag | ctcttaggga | cccaccattt | gccaactggg | ctctgccatg | 1967 |
| gccccaactc | tgttgagggc | atttccaccc | cacctatgct | gatctccccc | cctggaggcc | 2027 |
| tgggccactg | gtctctagca | ccccctcccc | tgccctgccc | cagGTAACTA | TGGCCTTCGG | 2087 |
| GATCAGCACA | TGGCCATTGC | TTGGGTGAAC | AGGAATATCG | CGGCCTTCGG | GGGGGACCCC | 2147 |
| AACAACATCA | CGCTCTTCGG | GGAGTCTGC | TGGAGGTGCCA | GCGTCTCTCT | GCAGgtctcc | 2207 |
| gggtaccgag | ctcgaattcg | attcgattct | atagtgtcac | ctaaatccaa | ttcactggcc | 2267 |
| agtcgtgttg | acaacgagga | gactgggaaa | accctggccg | ttacccaact | tgaatccgct | 2327 |
| ccgagcacat | cccctttccc | agctggctgg | atacggaaga | gcccgacgag | cccttccgaa | 2387 |
| cagg-----t | cggagtctcg | tgaggtcagc | tctctctgca | gctctggatc | ctgtggaggc | 2442 |
| ctgcccacag | ttgagagaag | cgcaacggaa | gggagggtgg | agaggacgtg | gagctggggc | 2505 |
| tgtggtgctg | gggtgtcctt | gtcccagcgt | ggggtgacgc | agagtgggga | gcggccttgg | 2562 |
| tgacgggatt | ctgggtcccg | tagACCCTCT | CCCCCTACAA | CAAGGGCCTC | ATCCGGCGAG | 2622 |
| CCATCAGCCA | GAGCGGCGTG | GCCCTGAGTC | CCTGGGTCAT | CCAGAAAAAC | CCACTCTTCT | 2682 |

*FIG. 3D*

| | | | | | | |
|---|---|---|---|---|---|---|
| GGGCCAAAAA | Ggtaaacagc | cccccgggca | gggctgggcg | gggccccggc | tgtccacatt | 2742 |
| tcccttcttt | atacctggcc | cccatccttg | ccggcctcac | cttacctgct | ggccttggtt | 2802 |
| ctgcccccag | GTGGCTGAGA | AGGTGGGTTG | CCCTGTGGGT | GATGCCGCCA | GGATGGCCCA | 2862 |
| GTGTCTGAAG | GTTACTGATC | CCCGAGCCCT | GACGCTGGCC | TATAAGGTGC | CGCTGGCAGG | 2922 |
| CCTGGAGTgt | gagtagctgc | tcgggttgcc | ccatggggtc | tcgagggggg | ggttgagggg | 2982 |
| ggtactccag | ggagtactcc | aggagagaag | gtaccagagc | tgcggtcttg | tactgtcacc | 3042 |
| aactagctgg | tgtctccctc | gaccccagct | gtaag----- | -agtgtcata | gatcagagaa | 3096 |
| ggaggagata | gccaattcca | cctgagagga | aggggctca | gggaaactgg | aggtacgaag | 3156 |
| aacctgctaa | cctgctggct | ctcccccagA | CCCCATGCTG | CACTATGTGG | GCTTCGTCCC | 3216 |
| TGTCATTGAT | GGAGACTTCA | TCCCCGCTGA | CCCGATCAAC | CTGTACGCCA | ACGCCGCCGA | 3276 |
| CATCGACTAT | ATAGCAGGCA | CCAACAACAT | GGACGGCCAC | ATCTTCGCCA | GCATCGACAT | 3336 |
| GCCTGCCATC | AACAAGGGCA | ACAAGAAAGT | CACGGAgtag | cgggggcaca | ggactcgggg | 3396 |
| cgtaccgtgg | ggagggcccg | ccgggaaaag | cactggcctg | gggccagcct | ggcggaggaa | 3456 |
| ggcaattgag | tcaggactgg | gagtcgaagt | tagcacggtc | gggtgagtat | gtgtcagtgc | 3516 |
| ccttaccttg | aattccccag | GGAGGACTTC | TACAAGCTGG | TCAGTGAGTT | CACAATCACC | 3576 |

*FIG. 3E*

AAGGGGCTCA GAGGCGCCAA GACGACCTTT GATGTCTACA CCGAGTCCTG GGCCCAGGAC 3636
CCATCCCAGG AGAATAAGAA GAAGACTGTG GTGGACTTTG AGACCGATGT CCTCTTCCTG 3696
GTGCCCACCG AGATTGCCCT AGCCCAGCAC AGAGCCAATG CCAAgtgagg atcttggcag 3756
cgggtggctc cttgggtcgg ctccttgggg ttcctgggtt cgcattccag ccgagtctcg 3816
ctgtgggtgg ctctaggtgt ggg--actct cttcatgtga tccacactcc ccccctgacc 3874
gatcctcaca tcagtcgtct ctggctgatc ggtcccagtg agaccctgcc tgcctacttg 3934
ggtggtctct ccccagGAGT GCCAAGACCT ACGCCTACCT GTTTTCCCAT CCCTCTCGGA 3994
TGCCCGTCTA CCCCAAATGG GTGGGGGCCG ACCATGCAGA TGACATTCAG TACGTTTTCG 4054
GGAAGCCCTT CGCCACCCCC ACGGGCTACC GGCCCCAAGA CAGGACAGTC TCTAAGGCCA 4114
TGATCGCCTA CTGGACCAAC TTTGCCAAAA CAGGgtaaga cgctgggcct tggagtgcag 4174
gctgagggca acagccgaga aggc------ cacagcccga tgcccagtat gcatggaggg 4228
tatggtccca gggctactag ctcagagggg tggggatggc tcaggcgtgc aggtgcagta 4288
gcaggcttca gcctcctggg agtccccgcc cctgcacagc ctcttctcac tctgcagGGA 4348
CCCCAACATG GGCGACTCGG CTGTGCCCAC ACACTGGGAA CCCTACACTA CGGAAAACAG 4408
CGGCTACCTG GAGATCACCA AGAAGATGGG CAGCAGCTCC ATGAAGCGGA GCCTGAGAAC 4468

*FIG. 3F*

```
CAACTTCCTG   CGCTACTGGA   CCCTCACCTA   TCTGGCGCTG   CCCACAGTGA   CCGACCAGGA   4528
GGCCACCCCT   GTGCCCCCCA   CAGGGGACTC   CGAGGCCACT   CCCGTGCCCC   CCACGGGTGA   4588
CTCCGAGACC   GCCCCCGTGC   CGCCCACGGG   TGACTCCGGG   GCCCCCCCCG   TGCCGCCCAC   4648
GGGTGACTCC   GGGGCCCCCC   CCGTGCCGCC   CACGGGTGAC   TCCGGGGCCC   gtaccccacc   4708
ttgggtgaca   ctgaggctga   ccccatcccc   gctacggtga   ctctgaggct   gcccccgtgc   4768
ccccctcagg   tgatctcgag   gctcccgcgt   acccctacgg   tgactct---   ccctctcatc   4825
tggagCCCCC   GTGCCGCCCA   CGGGTGACTC   CGGGGCCCCC   CCCGTGCCGC   CCACGGGTGA   4885
CTCCGGGGCC   CCCCCCGTGC   CGCCCACGGG   TGACTCCGGG   GCCCCCCCCG   TGCCGCCCAC   4945
GGGTGACTCC   GGCGCCCCCC   CCGTGCCGCC   CACGGGTGAC   GCCGGGCCCC   CCCCCGTGCC   5005
GCCCACGGGT   GACTCCGGCG   CCCCCCCCGT   GCCGCCCACG   GGTGACTCCG   GGGCCCCCCC   5065
CGTGACCCCC   ACGGGTGACT   CCGAGACCGC   CCCCGTGCCG   CCCACGGGTG   ACTCCGGGGC   5125
CCCCCCTGTG   CCCCCCACGG   GTGACTgtgc   atcg-----c   cggtgactct   gaggcccgtg   5180
cccgtgccca   ccttgggtga   gacactgagg   ctgccccatc   ccagCTGAGG   CTGCCCCTGT   5240
GCCCCCCACA   GATGACTCCA   AGGAAGCTCA   GATGCCTGCA   GTCATTAGGT   TTTAGCGTCC   5300
CATGAGCCTT   GGTATCAAGA   GGCCACAAGA   GTGGGACCCC   AGGGGCTCCC   CTCCCATCTT   5360
```

FIG. 3G

```
GAGCTCTTCC TGAATAAAGC CTCATACCCC Tgtcctggcg tctttctttg ctctcaaggg 5420
ctagctgacg gggagtggac ctcagttacc cttacagcac cagGGGGCCC AACTGTACCC 5480
ATCACCTGGT ACAAAAAAAA AAAAAAAGAA TTC                               5513
```

METHODS AND REAGENTS FOR RFLP ANALYSIS OF THE HUMAN PANCREATIC CHOLESTEROL ESTERASE GENE

This application is a continuation of U.S. Ser. No. 08/053,308, filed Apr. 26, 1993, now abandoned, which was a continuation of U.S. Ser. No. 07/730,204, filed Jul. 15, 1991, now abandoned.

BACKGROUND OF THE INVENTION

1. Field of the Invention

This invention relates to the human pancreatic cholesterol esterase gene. In particular, the invention relates to the identification of restriction fragment length polymorphisms (RFLP) of the human pancreatic cholesterol esterase gene. Specifically, the invention relates to the use of RFLP analysis for identifying individuals with a particular genetic variant of the human pancreatic cholesterol esterase gene. The invention also relates to development of methods for identifying individuals for appropriate treatment with therapeutic drugs for the prevention or alleviation of disease states in a human related to cholesterol metabolism.

Cholesterol metabolism is of critical interest to those involved in protecting human health. Atherosclerosis is the leading cause of death in the United States and reduction of serum cholesterol levels has recently been embraced as a national health priority. See NIH Consensus Panel Report, J.A.M.A. 253: 2094 (1985). NIH recommendations include measurement of serum cholesterol in all adults, with efforts to reduce cholesterol in those individuals with levels above 200 mg %. In this regard front line therapy is a reduction in the amount of cholesterol and triglycerides ingested, followed by the use of agents that interfere with absorption of ingested lipids. See Consensus Full Report, Arch. Inst. Med. 148: 36 (1988).

Since free cholesterol comprises about 90% of dietary cholesterol, it is not obvious that knowing either the phenotype or the genotype of the pancreatic cholesterol esterase gene would be useful. In fact, it had been thought prior to this time that cholesterol esterase was not important for cholesterol absorbsion [Huang and Hiu, J. Lipid Res. 31: 2029 (1991)]. Unexpectedly, pancreatic cholesterol esterase plays a pivotal role in the absorption of cholesterol and fatty acids (U.S. Pat. No. 5,017,565, issued May 21, 1991. Alterations in the genotype or phenotype of this enzyme may be a factor responsible for differences among individuals in susceptibility for developing cardiovascular disease and/or lipid abnormalities.

One way of investigating such genotypic alterations is the use of restriction fragment length polymorphism (RFLP) analysis. Using this technique, DNA polymorphisms can be detected as differences in the length of DNA fragments after digestion with DNA sequence-specific restriction endonucleases. Restriction fragments can then be separated by agarose gel electrophoresis, according to their molecular size, to reveal a pattern of RFLP-related bands. Differences in the length of a particular fragment may result from individual or multiple base substitutions, insertions or deletions. These genotypic changes can be recognized by the altered mobility of restriction fragments on agarose gel electrophoresis. Specific DNA sequences can then be detected by hybridization with a complimentary radioactive probe [see, for example, Botstein et al. Am. J. Hum. Genet. 32: 314–331 (1980)].

RFLP analysis has been used in studying a number of genes believed to be involved in either the absorbsion, transport or metabolism of cholesterol in vivo. These include the low density lipoprotein (LDL) cholesterol receptor gene relating to the diagnosis of familial hypercholesterolemia (FH) [see, for example, Lehrman et al., Proc. Natl. Acad. Sci. USA 83: 3679–3683 (1986); Hobbs et al., J. Clin. Invest. 81: 909–917 (1988); Daga et al., Hum. Genet. 84: 412–416] and the genes of apolipoproteins A-I, A-IV, and C-III [see, Karathanasis et al., Nature 304: 371–373 (1983); Karathanasis et al., Nature 305: 823–825 (1983); Shaw et al., Hum. Genet. 74: 267–269 (1986); Johansen et al., Clin. Genet. 37: 194–197 (1990); Funke et al., J. Clin. Invest. 87: 371–376 (1991)], all of which are associated with premature coronary heart disease [Antonakis, N.E.J.M. 320: 153–163 (1989)].

The present invention provides methods and reagents for detecting RFLPs in the human pancreatic cholesterol esterase gene. In addition, the invention provides methods and reagents for identifying RFLPs in this gene. Specifically, the invention relates to a RFLP in the gene that is related to a particular phenotype associated with the cholesterol esterase gene. This invention also provides methods and reagents for screening a human population for a particular RFLP and for identifying a target patient population for treatment of cholesterol esterase-related disease.

2. Information Disclosure Statement

Borja et al., Proc. J. Exp. Biol. and Med. 116: 496 (1964) teach that cholesterol esterase is secreted by the pancreas, and that its catalysis of cholesterol ester hydrolysis to produce free cholesterol and free fatty acids is essential for the absorption of cholesterol derived from cholesterol esters.

Botstein et al., Am. J. Hum. Genet. 32: 314–331 (1980) teach the use of restriction fragment length polymorphisms (RFLPS) for genetic mapping.

Norum et al., Physiol. Rev. 63: 1343–1419 (1983) review the biochemistry of cholesterol absorbsion and metabolism, including the role of pancreatic cholesterol esterase.

Karathanasis et al., Nature 304: 371–373 (1983) disclose RFLPs in the human apolipoprotein A-I and C-III genes.

Karathanasis et al., Nature 305: 823–825 (1983) disclose an RFLP in the human apolipoprotein A-I gene.

Lehrman et al., Proc. Natl. Acad. Sci. USA 83: 3679–3683 (1986) teach the association between an RFLP in the low density lipoprotein gene (LDL) and familial hypercholesterolemia (FH).

Bosner et al., Proc. Natl. Acad. Sci. USA 85: 7438–7442 (1988) teach that cholesterol esterase performs its function while anchored to the intestinal membrane via a receptor-like interaction with brush border membrane associated heparin.

Hobbs et al., J clin. Invest. 81: 909–917 (1988) disclose RFLPs associated with FH.

Cooper & Clayton, Hum. Genet. 78: 299–312 (1988) teach the use of RFLP analysis for the diagnosis of genetic disease and review the association between genetic polymorphism in apolipoprotein genes and atherosclerosis.

Ordovas & Schaefer, Ann. Biol. Clin. (Paris) 46: 24–29 (1988) teach the relationship between an RFLP in a PstI site in the human apolipoprotein A-I gene and coronary artery disease.

Kyger et al., Biochem. Biophys. Res. Comm. 164: 1302–1309 (1989) teach the nucleic acid sequence of a cDNA clone of bovine pancreatic cholesterol esterase.

Kissel et al., Biochim. Biophys. Acta 1006: 227–236 (1989) teach the nucleic acid sequence of a cDNA clone of mRNA encoding pancreatic cholesterol esterase of the rat.

Nilsson et al., Eur. J. Biochem. 192: 323–326 (1990) teach the nucleic acid sequence of a partial cDNA clone of human pancreatic cholesterol esterase.

Daga et al., Hum. Genet. 84: 412–416 (1990) disclose a RFLP in the LDL receptor gene associated with FH.

Johansen et al., Clin. Genet. 37: 194–197 (1990) disclose RFLPs in the apolipoprotein A-I/C-III gene cluster.

Berg, Acta Genet. Med. Gemellol. (Roma) 39: 15–24 (1990) review the association between RFLPs in human apolipoprotein genes and coronary heart disease.

Taylor et al., Genomics 10: 425–431 (1991) disclose the localization of the human cholesterol esterase gene to the terminal region of the long arm of chromosome 9.

Funke et al., J. Clin. Invest. 87: 371–376 (1991) disclose an RFLP in the human apolipoprotein A-I gene related to disease.

DESCRIPTION OF THE DRAWINGS

FIGS. 2A through 2G depict the cDNA sequence of the human cholesterol esterase gene, corresponding to sequence I.D. No. 12.

FIGS. 3A through 3G illustrate the genomic DNA sequence of the human cholesterol esterase gene, including sequences immediately flanking each of the 14 exons of the gene, corresponding to sequence I.D. Nos. 1–11, wherein uppercase letters represent exon sequences, lowercase letters represent intron sequences, and unsequenced portions of introns are represented by dashes (—).

BRIEF SUMMARY OF THE INVENTION

Figure 1:
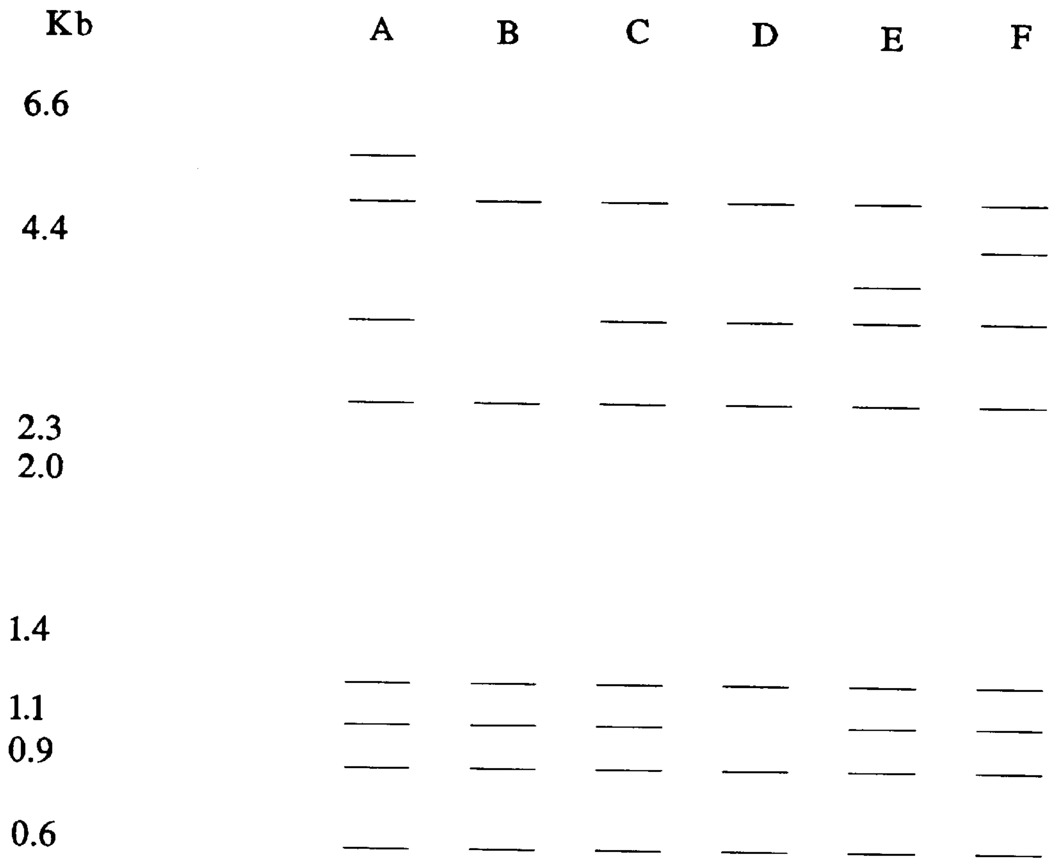
FIG. 1 illustrates RFLP patterns in the pancreatic cholesterol esterase gene generated by digestion of human. genomic DNA with the restriction enzyme StuI.

This invention relates to methods and reagents for the detection of restriction fragment length polymorphisms (RFLPS) in the human pancreatic cholesterol esterase gene, and the use of the detected patterns of particular RFLPs for screening human populations and identifying appropriate individuals for treatment with therapeutic drugs.

Cardiovascular disease is the leading cause of death in industrialized nations. Elevated serum cholesterol levels is a well known risk factor for the development and progression of atherosclerotic disease, particularly coronary heart disease. The absorption and metabolism of dietary cholesterol involves the action of various enzymes, among them pancreatic cholesterol esterase. Alterations in the genotype or phenotype of this enzyme may be a factor responsible for differences among individuals in susceptibility for developing cardiovascular disease and/or lipid abnormalities. One type of genetic polymorphism that may be associated with such susceptibility is restriction fragment length polymorphism (RFLP).

In a first aspect, this invention provides a method for detecting polymorphisms in the human pancreatic cholesterol esterase gene. Such detection is useful in light of the surprising revelations of the role of this enzyme in supporting the bulk of cholesterol absorbsion. This important role for pancreatic cholesterol esterase in intestinal cholesterol absorbsion was previously unrecognized (U.S. Pat. No. 5,017,565, issued May 21, 1991, which is hereby incorporated by reference).

The invention provides methods for detecting restriction fragment length polymorphisms in the human pancreatic cholesterol esterase gene. This method provides for digestion of a human DNA sample with a restriction enzyme and identification of the resulting pattern of fragments of the digested human DNA corresponding to the pancreatic cholesterol esterase gene. In a preferred embodiment, the restriction enzyme used in this digestion is StuI.

The invention also provides for a method for detecting RFLPs using the blot hybridization method of Southern [J. Mol. Biol. 98: 503–517 (1975)]. In this embodiment of the invention, a DNA sample is obtained from a human and the DNA digested with a restriction enzyme. The resulting fragments are separated into a pattern of bands according to size by electrophoresis in an agarose gel, transferred in the same pattern to a membrane and hybridized with a nucleic acid probe complementary to a portion of the pancreatic cholesterol esterase gene. In a preferred embodiment, the restriction enzyme used in this digestion is StuI. In another preferred embodiment, the probe is comprised of sequences essentially homologous to the nucleic acid sequence described in FIGS. 2A through 2G.

The invention further relates to the complete structure of the human pancreatic cholesterol esterase gene as illustrated in FIGS. 3A through 3G. The gene is comprised of 14 exons presented in uppercase type in FIGS. 3A through 3G; intron sequences immediately surrounding each exon are shown in lowercase type in FIGS. 3A through 3G and presented in Table 1.

The present invention also provides for the detection of RFLPs in the human pancreatic cholesterol esterase gene following amplification in vitro of regions surrounding the polymorphic restriction enzyme sites in the sample DNA. The invention provides for the in vitro amplification of any of the cholesterol esterase gene exons from DNA from a human, and determination of the nucleic acid sequence of that exon or the presence or absence of RFLPs in the exonic sequences. Determination of such sequences or RFLP profiles of the individual exons of the human cholesterol esterase gene can then be used as a screening procedure capable of correlating specific sequence markers with hyper- and hypoactivity of human cholesterol esterase.

Thus, an object of the present invention is to provide a method for screening a human population to determine the frequency of different RFLPs in the pancreatic cholesterol esterase gene. As a consequence of the use of the methods provided by the present invention, the distribution of different RFLPs in the human population can be determined statistically. These statistics can then be used to establish correlations between the occurrence of particular RFLPs and the susceptibility or resistance of individuals carrying these RFLPs to cardiovascular disease, elevated serum cholesterol levels and the absorption and metabolism of dietary cholesterol.

In another embodiment, the invention provides for determining the existence of a particular RFLP within the human pancreatic cholesterol esterase gene of an individual human by comparison of the pattern of restriction fragments generated using a particular restriction enzyme to the patterns exhibited in a representative panel of human DNA samples digested with the same restriction enzyme. In a preferred embodiment, the restriction enzyme is StuI. In an additional preferred embodiment, the representative panel patterns used for these comparisons are the patterns depicted in FIG. 1.

The present invention provides for a method of identifying a human target population for administration of a therapeutic drug for the prevention or alleviation of disease states in a human related to cholesterol absorbsion or metabolism.

In this embodiment, the RFLP pattern of the target population is compared with the patterns exhibited in a representative panel of RFLPs, this panel being composed of members at least one of which will indicate a correlation with the appropriateness of administration of a particular therapeutic drug. The choice of therapeutic administration of the drug is then made on the basis of this correlation and the pattern of RFLPs in the individuals of the human target population. In a preferred embodiment, the restriction enzyme is StuI. In an additional preferred embodiment, the representative panel patterns used for these comparisons are the patterns depicted in FIG. 1.

The invention also provides reagents for the detection of restriction fragment length polymorphisms in the human pancreatic cholesterol esterase gene. The reagents provided by the invention include nucleic acid sequences complementary to a portion of the sequence of the human pancreatic cholesterol esterase gene. In a preferred embodiment, the reagent is essentially homologous to the sequence described in FIGS. 2A through 2G.

The invention also provides reagents for the screening of restriction fragment length polymorphisms in the human pancreatic cholesterol esterase gene. The reagents provided by the invention include nucleic acid sequences complementary to a portion of the sequence of the human pancreatic cholesterol esterase gene. In a preferred embodiment, the reagent is essentially homologous to the sequence described in FIGS. 2A through 2G.

The invention also provides reagents for determining the presence of restriction fragment length polymorphisms in the human pancreatic cholesterol esterase gene. The reagents provided by the invention include nucleic acid sequences complementary to a portion of the sequence of the human pancreatic cholesterol esterase gene. In a preferred embodiment, the reagent is essentially homologous to the sequence described in FIGS. 2A through 2G.

The invention also provides reagents for identifying a human target population for administration of a therapeutic drug for the prevention or alleviation of disease states in a human related to cholesterol metabolism. The reagents provided by the invention include nucleic acid sequences complementary to a portion of the sequence of the human pancreatic cholesterol esterase gene. In a preferred embodiment, the reagent is essentially homologous to the sequence described in FIGS. 2A through 2G.

Specific preferred embodiments of the present invention will become evident from the following more detailed description of certain preferred embodiments and the claims.

DETAILED DESCRIPTION OF THE PREFERRED EMBODIMENTS

This invention provides methods and reagents for detecting RFLPs in the human cholesterol esterase gene, and methods for screening human populations for such RFLPs and identifying appropriate individuals for treatment with therapeutic drugs.

DNA samples used according to the invention include but are not limited to DNA from normal, diseased or malignant human cells, either extracted or derived from living or postmortem tissues, organs or fluids; germinal cells including sperm and egg cells, or zygotes, embryos, chorionic or amniotic cells; cells grown in vitro, from either long-term or short-term culture, and either normal, immortalized or transformed; or any forensic material, including but not limited to semen, blood, hair or other samples. In a preferred embodiment, DNA is obtained from human leukocyte cells.

DNA samples used according to the present invention will be isolated from the abovenamed sources so as to be essentially undegraded. It will be understood by those with skill in the art that by "essentially undegraded" is meant that the DNA samples will be of sufficient integrity that RFLPs of single copy genes will be detectable by the methods of the invention. Essentially undegraded DNA is isolated by mean well known to those with skill in the art.

DNA samples used according to the invention are digested with restriction enzymes. Restriction enzymes used according to the invention are comprised of all Type I and Type II restriction enzymes. These include but are not limited to enzymes that recognize eight basepairs (e.g., NotI, SfiI), six basepairs (e.g., EcoRI, BamHI, HindIII), 5 basepairs (e.g., HincII, HinfI) or 4 basepairs (e.g., TaqI, MboI, Sau3A); enzymes that are (HpaII, SmaI) or are not (MspI, XmaI) inhibited by methylation of bases in their recognition site; and synthetic restriction enzymes of unique specificity. In a preferred embodiment, the invention provides the enzyme StuI, which has the base recognition sequence AGG/CCT.

Polymorphic DNA fragments generated by restriction enzyme digestion are separated for analysis according to the methods of the invention. The methods used for such separation include but are not limited to electrophoresis and chromatography. Electrophoretic methods according to the invention are performed using a variety of separation media including gels comprised of agarose, acrylamide or any mixture of these components.

After separation, the polymorphic fragments generated according to the invention are transferred in the same pattern from the separation media onto a membrane for hybridization. Membranes used according to the invention include but are not limited to nitrocellulose membranes and nylon membranes. Methods of transferring the polymorphic fragments include but are not limited to capillary and electrophoretic means well know to those with skill in the art. Hybridization of polymorphic fragments bound to such membranes is performed using techniques well known to the skilled.

The present invention also provides reagents for the detection of RFLPs in the pancreatic cholesterol esterase gene. The reagents are comprised of probes for detecting polymorphic fragments of the cholesterol esterase gene. The probes include but are not limited to nucleic acid sequences essentially homologous to portions of the sequence depicted in FIGS. 2A through 2G. For purposes of this invention, the term "essentially homologous" is intended to mean that at least 70% of the nucleic acid sequence provided is identical to the corresponding portion of the sequence depicted in FIG. 2. Such sequences will hybridize with the corresponding sequences of the pancreatic cholesterol esterase gene present in genomic DNA under conditions of high stringency as provided by the methods of the invention. Such sequences provided by the invention can be either single stranded or double stranded, and includes oligonucleotides whose sequences are derived from the sequence depicted in FIGS. 2A through 2G and that are made either in vivo or in vitro using techniques well known to those with skill in the art. The probes provided by the present invention also include sequences chemically synthesized by methods known to the skilled. The probes provided by the present invention also include sequences synthesized by in vitro amplification of template sequences derived from DNA or RNA that are essentially homologous to the sequences depicted in FIGS. 2A through 2G. In a preferred embodiment, the reagent provided by the invention is a complementary DNA (cDNA) clone of human pancreatic cholesterol esterase mRNA whose sequence is essentially homologous to the sequence depicted in FIGS. 2A through 2G.

Probes provided by the present invention may be labeled to enable their detection after hybridization. Labels used include but are not limited to radioactive labels (e.g., $^{32}P$-labeled dCTP), fluorescent labels [e.g., fluorescein isothiocyanate (FITC)-labeled dCTP] and antigenic labels (e.g., biotinylated dUTP). Such labels are detected using techniques appropriate for detecting each label, including but not limited to autoradiography, fluorescence or by well-known immunologically-based techniques.

The invention also provides patterns of polymorphic DNA fragments detected following hybridization with DNA of homologous to the human pancreatic cholesterol esterase gene. These patterns reflect the genetic polymorphisms revealed by RFLP analysis. Panels is of such patterns may then be used to correlate particular RFLPs in the gene with a specific phenotype. In a preferred embodiment, the present invention provides an RFLP pattern of the human pancreatic cholesterol esterase gene that is associated with a particular cholesterol absorbsion and utilization phenotype.

The information obtained using the methods of the present invention may be used to identify a target population for treatment using a therapeutic drug for the prevention or alleviation of disease states in a human related to cholesterol metabolism. In a preferred embodiment, the therapeutic drug is an inhibitor of human pancreatic cholesterol esterase.

The invention further relates to the complete structure of the human pancreatic cholesterol esterase gene as illustrated in FIGS. 3A through 3G. The gene is comprised of 14 exons; intron sequences immediately surrounding each exon are shown in FIGS. 3A through 3G and presented in Table 1. The heparin binding site of the protein (KKRCLQ) is encoded in exon 4. The active site serine and surrounding sequences (GESAG) is encoded in exon 6. The polymorphic StuI site is found in exon 8. The heparin inhibitory site is encoded in exon 9. The active site histidine residue is encoded in exon 11. The meaning of the single letter abbreviations for each amino acid is provided in Table 2.

The present invention also provides for the detection of RFLPs in the human pancreatic cholesterol esterase gene following amplification in vitro of regions surrounding the polymorphic restriction enzyme sites in the sample DNA. Primer sequences homologous to intron sequences flanking each exon are made using methods well known to those with skill in the art. Appropriate primer pairs can then be used to amplify each exon in vitro using well-known methods. The sequence of DNA fragments so amplified can be determined, or alternatively these DNA fragments can be analyzed by restriction enzyme digestion to disclose the presence or absence of diagnostic RFLPs.

The invention thus enables in vitro amplification and analysis of any of the cholesterol esterase gene exons from DNA from a human. Analysis of the amplified exon sequences can then be used as a screening procedure capable of correlating specific sequence markers with hyper- and hypoactivity of human cholesterol esterase.

The following examples are shown by way of illustration and not by way of limitation.

TABLE I

| 3' Exon | 5' Intron | 3' Intron | 5' Exon | Exon # | Size (bp) |
|---|---|---|---|---|---|
| TATTCATCCA | gt ................................ | gaggggggatcccct ag | GAGGCTGATG | 2 | 81 |
| TGCCGCGAAG | gt aagagccagcgga.................. | gcccgtgtctccctcgc ag | CTGGGCGCCG | 3 | 151 |
| GGCTGGCAAG | gt gggtggtgtccgccac.............. | ccaactcctgccacctgc ag | GGACCCTGAA | 4 | 123 |
| AGGAAGCAAG | gt ctgcctcccctctact............... | agcccgtcccccatctc ag | TCTCCCGGGA | 5 | 198 |
| AATCTGCCAG | gt gccgatgggtgggccgaa............. | tcccctgccctgccccc ag | GTAACTATGG | 6 | 131 |
| CTCTCTGCAG | gt ctccgggtaccgagctcgaa........... | ggatttctgggtcccgt ag | ACCCTCTCCC | 7 | 108 |
| GGGCCAAAAG | gt aaacacccccgggcaggg............... | ttggttctgccccc ag | GTGGCTGAGA | 8 | 118 |
| GGCCTGGAGT | gt gagtagctgctcgggttg............. | cctgctggctctccccc ag | CCCCATGCTG | 9 | 187 |
| AAGTCACGGA | gt agcgggggcacaggactcggggc......... | ttaccttgaattcccc ag | GGAGGACTTC | 10 | 204 |
| CCAATGCCAA | gt gaggatcttggcagcggg............... | gggtggtctctcccc ag | GAGTGCCAAG | 11 | 198 |
| CCAAAACAGG | gt aagacgctgggccttggag............. | cctcttctcactctgc ag | GGACCCAACA | 12 | 353 |
| CCGGGGCCCC | gt taccccaccttgggtg................... | ccctctcatctcc ag | CCCCCGTGCC | 13 | 321 |
| ACGGGTGACT | gt gcatcggggccatgg................. | gaggctgccccatccc ag | CTGAGGCTGC | 14 | 167 |
| TCATACCCCT | gt cctggcgtctttcttgctct...... | | | | |

TABLE II

| Amino Acid | Abbreviation |
|---|---|
| Alanine | A |
| Arginine | R |
| Aspartic acid | D |
| Asparagine | N |
| Cysteine | C |
| Glutamic acid | E |
| Glutamine | Q |
| Glycine | G |
| Histidine | H |
| Isoleucine | I |
| Leucine | L |
| Lysine | K |

TABLE II-continued

| Amino Acid | Abbreviation |
|---|---|
| Methionine | M |
| Phenylalanine | F |
| Proline | P |
| Serine | S |
| Threonine | T |
| Tryptophan | W |
| Tyrosine | Y |
| Valine | V |

EXAMPLE 1

RFLP Analysis of the Human Pancreatic Cholesterol Esterase Gene

A pattern of pancreatic cholesterol esterase-associated RFLPs in human DNA was determined.

The population studied comprised ninety six healthy adults. Thirty milliliters of venous blood was obtained after an overnight fast, part of which was used for the determination of total cholesterol (TC), Low Density Lipoprotein (LDL) Cholesterol, High Density Lipoprotein (HDL) Cholesterol, Very Low Density Lipoprotein (VLDL) Cholesterol, and Triglycerides (TG); the rest of the blood was used to isolate DNA from lymphocytes as described in Maniatis et al., 1982, *Molecular Cloning: A Laboratory Manual* (Cold spring Harbor Press: N.Y.). Briefly, human white blood cells (leukocytes), consisting primarily of lymphocytes, were separated from red blood cells into a buffy coat layer by centrifugation. The cells were washed once with phosphate buffered saline (PBS) and lysed in a solution of 1% sodium dodecyl sulfate (SDS) and 50 μg/ml proteinase K. Cellular proteins were digested overnight at 50° C. Nucleic acid was purified from digested and residual protein by sequential extractions with buffer-equilibrated phenol, phenol:chloroform:isoamyl alcohol (24:24:1) and chloroform:isoamyl alcohol (24:1) and then precipitated by the addition of 2.5 volumes of absolute ethanol. The precipitated nucleic acid was spooled from the solution, dried and resuspended in 10 mM Tris-HCl/1 mM ethylenediamine-tetraacetic acid (1X TE). A solution of 10 mg/ml RNase was added to a final concentration of 20 μg/ml and the RNA in the solution was digested for 1 hour at 37° C. The solution was extracted with organic reagents as described above, and the DNA precipitated with ethanol. The concentration of DNA after resuspending in 1X TE was determined by ultraviolet spectroscopy.

Ten μg of DNA were digested with the restriction enzyme StuI (Promega, Madison, Wis.) overnight at room temperature, and the digested DNA was then electrophoresed through a 0.8% agarose gel (FMC, Rockland, Me.) in Tris-acetate-EDTA buffer (pH 7.8) at 3 volts/cm for about 16 hours. After staining with ethidium bromide and visualization of the digested genomic DNA (which appears as a smear), gels were blotted onto a nylon membrane (MSI, Westboro, Me.) by the method of Southern (supra). The blots were hybridized overnight at 68° C. with a human pancreatic cholesterol esterase complimentary DNA (cDNA) probe which had been labeled with $^{32}$-dCTP by the random priming method of Feinberg and Vogelstein [Anal. Biochem. 132: 6 (1983)] using reagents supplied by Boehringer Mannheim (Indianapolis, Ind.). The blots were washed after hybridization to a stringency of 0.2X standard saline-citrate (SSC; 0.15M NaCl/0.015M Na-citrate, pH 7.0) and 0.1% SDS at the temperature used for hybridization. The membranes were exposed to X-ray film (X-OMat AR50; Eastman Kodak Co., Rochester, N.Y.) at −70° C. for up to 7 days before development.

Representative patterns of RFLPs obtained using these methods are depicted in FIG. 1. Six distinct patterns of restriction fragments were obtained at the following frequencies:

| Pattern | Frequency |
|---|---|
| A | 1.5% |
| B | 34% |
| C | 49% |
| D | 12% |
| E | 1.5% |
| F | 2% |

EXAMPLE 2

Statistical Analysis of RFLP Frequencies

The patterns of RFLPs obtained in Example 1 were analyzed with reference to the total cholesterol (TC), Low Density Lipoprotein (LDL) Cholesterol, High Density Lipoprotein (HDL) Cholesterol, Very Low Density Lipoprotein (VLDL) Cholesterol, and Triglycerides (TG) present in each blood sample, as well as by age and gender. The results of these statistical analyses are presented in Tables III–V. Univariate analysis of age and sex adjusted variables was used for statistical evaluation. Five percent was chosen as the level of significance.

Table III shows the TC, LDL, HDL, VLDL and TG values associated with each RFLP pattern. The numbers in parentheses adjacent to each value are the number of individuals of each gender and RFLP averaged to yield that value. Table IV shows the age and sex adjusted variables of the effect of RFLP pattern C on lipid and lipoprotein values. Table V shows the distribution of LDL and HDL values on the basis of pattern and gender.

Male patients of RFLP pattern C tended to have a lower LDL cholesterol that non-pattern C males (p=0.07); this relationship remained after correction for age. This conclusion is supported by the fact that eighty percent of all males with LDL cholesterol under 100 mg/dl were found to exhibit pattern C. No differences were found in the LDL cholesterol between pattern C and non-pattern C females. Since it is well known that significant differences exist in HDL cholesterol between males and females, correction for both sex and age effects on these values were carried out. Analysis of variance suggested that while there were no significant differences in adjusted HDL cholesterol levels between pattern C and non-pattern C individuals, there was a significant interaction of the pattern type with sex (p=0.03); the HDL cholesterol being highest in males of pattern C and lowest in females of the same RFLP pattern.

No association was found between the RFLP pattern and total cholesterol, triglycerides, and very low density lipoprotein cholesterol.

The results of this analysis can be summarized as follows: the male patients with the RFLP pattern C contained the majority of male patients with lower LDL cholesterol levels; their HDL cholesterol was also the highest when compared to non-pattern C males. Although the females with pattern C had the lowest HDL cholesterol levels, their LDL cholesterol was not different than that of non-pattern C females.

Thus, unexpectedly, the group C genotype in males is associated with a favorable lipid phenotype (i.e., low LDL and high HDL) and these males would therefore not be candidates for treatment with inhibitors of cholesterol esterase.

TABLE III

| | A | B | C | D | E | F |
|---|---|---|---|---|---|---|
| TC M | 170(1) | 201 ± 29(9) | 189 ± 41(20) | 203 ± 50(6) | 196(1) | 248(1) |
| F | — | 194 ± 52(24) | 198 ± 38(27) | 209 ± 28(6) | — | 249(1) |
| Mean | 170 | 196 ± 47 | 194 ± 40 | 206 ± 39 | 196 | 248 |
| LDL M | 104 | 127 ± 22 | 109 ± 27 | 135 ± 41 | 131 | — |
| F | — | 111 ± 49 | 118 ± 36 | 120 ± 27 | — | 152 |
| Mean | 104 | 115 ± 44 | 114 ± 32 | 127 ± 34 | 131 | 152 |
| HDL M | 33 | 47 ± 10 | 47 ± 9 | 42 ± 8 | 43 | 29 |
| F | — | 58 ± 16 | 53 ± 12 | 68 ± 16 | — | 71 |
| Mean | 33 | 55 ± 15 | 50 ± 10 | 55 ± 18 | 43 | 50 ± 27 |
| TG M | 166 | 136 ± 39 | 148 ± 96 | 133 ± 67 | 112 | 413 |
| F | — | 115 ± 77 | 135 ± 74 | 106 ± 29 | — | 129 |
| Mean | 166 | 121 ± 69 | 141 ± 84 | 119 ± 51 | 112 | 271 ± 201 |
| VLDL M | 33 | 27 ± 8 | 24 ± 11 | 26 ± 13 | 22 | — |
| F | — | 20 ± 10 | 27 ± 14 | 21 ± 6 | — | 26 |
| Mean | 33 | 22 ± 10 | 26 ± 12 | 24 ± 10 | 22 | 26 |

TABLE IV

EFFECT OF C VS. NON-C PATTERN TYPE ON AGE AND SEX ADJUSTED LIPID AND LIPOPROTEIN VARIABLES

| | Pattern | | Pattern x Sex | |
|---|---|---|---|---|
| | F-value | P | F-value | P |
| T.C. | 0.35 | 0.56 | 0.51 | 0.48 |
| LDL | 1.19 | 0.28 | 2.88 | 0.09 |
| HDL | 0.06 | 0.81 | 4.68 | 0.03 |
| TG | 0.57 | 0.45 | 0.69 | 0.41 |
| VLDL | 1.13 | 0.29 | 2.17 | 0.14 |

TABLE V

DISTRIBUTION OF LDL AND HDL CHOLESTEROL BY PATTERN AND SEX

| | | MEAN(mg/dl) | S.D. | n |
|---|---|---|---|---|
| LDL CHOLESTEROL | | | | |
| PATTERN C | MALES | 109 | 26.6 | 19 |
| | FEMALES | 118 | 35.8 | 27 |
| NON-PATTERN C | MALES | 125 | 28.8 | 19 |
| | FEMALES | 114 | 45.0 | 31 |
| HDL CHOLESTEROL | | | | |
| PATTERN C | MALES | 47 | 9.5 | 20 |
| | FEMALES | 53 | 11.7 | 27 |
| NON-PATTERN C | MALES | 44 | 9.3 | 20 |
| | FEMALES | 60 | 15.9 | 31 |

What is claimed is:

1. A method for detecting a restriction fragment length polymorphism in a gene encoding pancreatic cholesterol esterase in a human comprising the following steps:

(a) isolating a sufficient quantity of DNA from the human;

(b) digesting the DNA with a restriction enzyme that is the restriction enzyme StuI to produce a multiplicity of fragments of digested DNA;

(c) separating the fragments of digested DNA on a separation medium;

(d) transferring the separated fragments of digested DNA onto a membrane;

(e) hybridizing the separated fragments of digested DNA with a detectably-labeled nucleic acid probe complementary to a portion of the human pancreatic cholesterol esterase gene, said probe comprising a nucleic acid sequence identified as SEQ ID No.: 12, wherein the probe comprises a nucleic acid having the sequence of exon 8 of the human pancreatic cholesterol esterase gene (SEQ ID No.: 6), and under hybridization conditions wherein the probe hybridizes specifically to the DNA fragments comprising the human pancreatic cholesterol esterase gene; and (f) detecting a pattern of the hybridized fragments of the human pancreatic cholesterol esterase gene that is one of the patterns depicted in FIG. 1.

2. The method of claim 1 wherein the DNA isolated from the human is derived from human leukocytes.

3. The method of claim 1 wherein the fragments are separated by electrophoresis.

4. The method of claim 1 wherein the fragments are separated by chromatography.

5. The method of claim 1 wherein the separation medium is an agarose gel.

6. The method of claim 1 wherein the separation medium is an acrylamide gel.

7. The method of claim 1 wherein the membrane is selected from the group comprised of nitrocellulose membranes and nylon membranes.

8. The hybridization probe of claim 1 wherein the probe is detectably labeled with a radioactive label, a fluorescent label or an antigenic label.

9. The method of claim 1 wherein the pattern of hybridized fragments of the human pancreatic cholesterol esterase gene are detected by autoradiography.

10. A method for determining the presence of a restriction fragment length polymorphism in a gene encoding pancreatic cholesterol esterase in an individual human comprising the following steps:

(a) detecting a pattern of DNA fragments of the gene encoding pancreatic cholesterol esterase in the individual human according to the method of claim 1; and (b) comparing the pattern detected in the DNA of an individual human with the patterns of a representative panel of restriction fragment length polymorphisms in the human pancreatic cholesterol esterase gene, said panel depicted in FIG. 1.

11. A reagent for detecting a restriction fragment length polymorphism in a gene encoding pancreatic cholesterol esterase in a human comprising an isolated and purified nucleic acid consisting of the nucleotide residue sequence as set forth in SEQ ID NO. 12 and degenerate variants thereof.

* * * * *

```
                    SEQUENCE LISTING


(1) GENERAL INFORMATION:

   (iii) NUMBER OF SEQUENCES: 13


(2) INFORMATION FOR SEQ ID NO:1:

     (i) SEQUENCE CHARACTERISTICS:
          (A) LENGTH: 98 base pairs
          (B) TYPE: nucleic acid
          (C) STRANDEDNESS: single
          (D) TOPOLOGY: linear

    (ii) MOLECULE TYPE: DNA (genomic)

    (ix) FEATURE:
          (A) NAME/KEY: exon
          (B) LOCATION: 1..96

    (ix) FEATURE:
          (A) NAME/KEY: intron
          (B) LOCATION: 97..98
```

-continued (xi) SEQUENCE DESCRIPTION: SEQ ID NO:1:

GAATTCCGGA TCAATACAGT TTACCTTCTG TATCAGTTAA GTGTCAAGAT GGAAGGAACA 60

GCAGTCTCAA GATAATGCAA AGAGTTTATT CATCCAGT 98

(2) INFORMATION FOR SEQ ID NO:2:

(i) SEQUENCE CHARACTERISTICS:
(A) LENGTH: 401 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: intron
(B) LOCATION: 1..137

(ix) FEATURE:
(A) NAME/KEY: exon
(B) LOCATION: 138..219

(ix) FEATURE:
(A) NAME/KEY: intron
(B) LOCATION: 220..401

(xi) SEQUENCE DESCRIPTION: SEQ ID NO:2:

TGATCAAGCG GTCAAACATG ACGACATTCG CGCCCAGACA ATAAGAGTAC AGACGTGCAA 60

GCGTAAGTGA GGGAAGTGCC TAGGCTCGCG ATGAGAGTAA GTAGCCTCGG AGGCCCAGGG 120

GGAGGGGGAT CCCCTAGGAG GCTGATGCTC ACCATGGGGC GCCTGCAACT GGTTGTGTTG 180

GGCCTCACCT GCTGCTGGGC AGTGGCGAGT GCCGCGAAGG TAAGAGCCCA GCGGAGGGGC 240

AGGTCCTGCT GCTCTCTCGC TCAATCAGAT CTGGAAACTT CGGGCCAGGC TGAGAAAGAG 300

CCCAGCACAG CCCCGCAGCA GATCCCGGGC ACTACCGTCA TTTCTATGGG ACAGGTGCCA 360

GGTAGAACAC GGATGCCAAT TCCATTTGAA TTTCAGATAA C 401

(2) INFORMATION FOR SEQ ID NO:3:

(i) SEQUENCE CHARACTERISTICS:
(A) LENGTH: 553 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: intron
(B) LOCATION: 1..282

(ix) FEATURE:
(A) NAME/KEY: exon
(B) LOCATION: 283..433

(ix) FEATURE:
(A) NAME/KEY: intron
(B) LOCATION: 434..553

(xi) SEQUENCE DESCRIPTION: SEQ ID NO:3:

AACCCAACCT CCATCCCACC TCTTGGCCGG CTTCCCTAGT GGGAACACTG GTTAACCAGT 60

TTTCCTCTAA GATTCTGGAG CAGACACCCC AGGGATAAGA GAGGAACAGG AATCCTAAAG 120

CCCTGAGCAT TGCAGGGCAG GGGGTGCTGC CTGGGTCTCC TGTGCAGAGC TGTCCTGCTT 180

TGAAGCTGTC TTTGCCTCTG GGCACGCGGA GTCGGCTTCC TTGCCCCTGG GATTCAGGCC 240

GATGGCTTGA GCCCCCTGAC CCTGCCCGTG TCTCCCTCGC AGCTGGGCGC CGTGTACACA 300

-continued

GAAGGTGGGT TCGTGGAAGG CGTCAATAAG AAGCTCGGCC TCCTGGGTGA CTCTGTGGAC 360

ATCTTCAAGG GCATCCCCTT CGCAGCTCCC ACCAAGGCCC TGGAAAATCC TCAGCCACAT 420

CCTGGCTGGC AAGGTGGGTG GTGTCCGCCA CTCCCCTCCG GGGGGTAAGG CCCCGGTTCC 480

TTCCTCATGC CAACTCCGGT CCACCGTCAG GACCCTAAGG CAAGAACTTC AAGAGAATCT 540

CCAGCACCAT ACC 553

(2) INFORMATION FOR SEQ ID NO:4:

(i) SEQUENCE CHARACTERISTICS:
(A) LENGTH: 719 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: intron
(B) LOCATION: 1..76

(ix) FEATURE:
(A) NAME/KEY: exon
(B) LOCATION: 77..199

(ix) FEATURE:
(A) NAME/KEY: intron
(B) LOCATION: 200..474

(ix) FEATURE:
(A) NAME/KEY: exon
(B) LOCATION: 475..672

(ix) FEATURE:
(A) NAME/KEY: intron
(B) LOCATION: 673..719

(xi) SEQUENCE DESCRIPTION: SEQ ID NO:4:

AGTGGGTGGT GAGGACTGGC TGGGGGGGGG GGGGTGAGGG GGCTGCCTTC CTCATGCCAA 60

CTCCTGCCAC CTGCAGGGAC CCTGAAGGCC AAGAACTTCA AGAAGAGATG CCTGCAGGCC 120

ACCATCACCC AGGACAGCAC CTACGGGGAT GAAGACTGCC TGTACCTCAA CATTTGGGTG 180

CCCCAGGGCA GGAAGCAAGG TCTGCCTCCC CTCTACTCCC AAGGACCCTC CCATGCAGCC 240

CACTGCCCCG GGTCTACTCC TGGCTTGAGT CTGGGGGCTG CAAAGCTGAA CTTCCATGAA 300

ATCCCACAGA GGCGGGGAGG GGAGCGCCCA CTGCCGTTGC CCAGCCTGGG GCAGGGCAGC 360

GCCTTGGAGC ACCTCCCTGT CTTGGCCCCA GGCACCTGCT GCACAGGGAC AGGGACCGGC 420

TGGAGACAGG GCCAGGCGGG GCGTCTGGGG TCACCAGCCG CTCCCCCATC TCAGTCTCCC 480

GGGACCTGCC CGTTATGATC TGGATCTATG GAGGCGCCTT CCTCATGGGG TCCGGCCATG 540

GGGCCAACTT CCTCAACAAC TACCTGTATG ACGGCGAGGA GATCGCCACA CGCGGAAACG 600

TCATCGTGGT CACCTTCAAC TACCGTGTCG GCCCCCTTGG GTTCCTCAGC ACTGGGGACG 660

CCAATCTGCC AGGTCCTGAG GTGGGCCGAA ACCAGCATGA GGGAGCAGGG AGATTTCAT 719

(2) INFORMATION FOR SEQ ID NO:5:

(i) SEQUENCE CHARACTERISTICS:
(A) LENGTH: 621 base pairs
(B) TYPE: nucleic acid
(C) STRANDEDNESS: single
(D) TOPOLOGY: linear (ii) MOLECULE TYPE: DNA (genomic)

-continued (ix) FEATURE:
(A) NAME/KEY: intron
(B) LOCATION: 1..300

(ix) FEATURE:
(A) NAME/KEY: exon
(B) LOCATION: 301..431

(ix) FEATURE:
(A) NAME/KEY: intron
(B) LOCATION: 432..621

(xi) SEQUENCE DESCRIPTION: SEQ ID NO:5:

AAATGAGAAG AGATGGGTAG GGAGACAGTG ATGGCTGACA TCTAAAACAC CCCCTAGACA 60

CACCAACCCA ACCTCCTGGA ACCCACCCAT ACAGCACCGA ACCCAGCTCA GCCTAGTCTC 120

CTGGGACCCA CCCCCTCCAG CACCCTACCC GACCCAGCTC TTAGGGACCC ACCATTTGCC 180

AACTGGGCTC TGCCATGGCC CCAACTCTGT TGAGGGCATT TCCACCCCAC CTATGCTGAT 240

CTCCCCCCCT GGAGGCCTGG GCCACTGGTC TCTAGCACCC CCTCCCCTGC CCTGCCCCAG 300

GTAACTATGG CCTTCGGGAT CAGCACATGG CCATTGCTTG GGTGAAGAGG AATATCGCGG 360

CCTTCGGGGG GGACCCCAAC AACATCACGC TCTTCGGGGA GTCTGCTGGA GGTGCCAGCG 420

TCTCTCTGCA GGTCTCCGGG TACCGAGCTC GAATTCGATT CGATTCTATA GTGTCACCTA 480

AATCCAATTC ACTGGCCAGT CGTGTTGACA ACGAAGAGAC TGGGAAAACC CTGGCCGTTA 540

CCCAACTTGA ATCCGCTCCG AGCACATCCC CTTTCCCAGC TGGCTGGATA CGGAAGAGCC 600

CGACGAGCCC TTCCGAACAG G 621

(2) INFORMATION FOR SEQ ID NO:6:

(i) SEQUENCE CHARACTERISTICS:
(A) LENGTH: 686 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: intron
(B) LOCATION: 1..194

(ix) FEATURE:
(A) NAME/KEY: exon
(B) LOCATION: 195..302

(ix) FEATURE:
(A) NAME/KEY: intron
(B) LOCATION: 303..421

(ix) FEATURE:
(A) NAME/KEY: exon
(B) LOCATION: 422..539

(ix) FEATURE:
(A) NAME/KEY: intron
(B) LOCATION: 540..686

(xi) SEQUENCE DESCRIPTION: SEQ ID NO:6:

TCGGAGTCTC GTGAGGTCAG CTCTCTCTGC AGCTCTGGAT CCTGTGGAGG CCTGCCCACA 60

GTTGAGAGAA GCGCAACGGA AGGGAGGGTG GAGAGGACGT GGAGCTGGGG CTGTGGTGCT 120

GGGGTGTCCT TGTCCCAGCG TGGGGTGACG CAGAGTGGGG AGCGGCCTTG GTGACGGGAT 180

TCTGGGTCCC GTAGACCCTC TCCCCCTACA ACAAGGGCCT CATCCGGCGA GCCATCAGCC 240

AGAGCGGCGT GGCCCTGAGT CCCTGGGTCA TCCAGAAAAA CCCACTCTTC TGGGCCAAAA 300

```
AGGTAAACAG CCCCCCGGGC AGGGCTGGGC GGGGCCCCGG CTGTCCACAT TTCCCTTCTT      360

TATACCTGGC CCCCATCCTT GCCGGCCTCA CCTTACCTGC TGGCCTTGGT TCTGCCCCCA      420

GGTGGCTGAG AAGGTGGGTT GCCCTGTGGG TGATGCCGCC AGGATGGCCC AGTGTCTGAA      480

GGTTACTGAT CCCCGAGCCC TGACGCTGGC CTATAAGGTG CCGCTGGCAG GCCTGGAGTG      540

TGAGTAGCTG CTCGGGTTGC CCCATGGGGT CTCGAGGGGG GGGTTGAGGG GGGTACTCCA      600

GGGAGTACTC CAGGAGAGAA GGTACCAGAG CTGCGGTCTT GTACTGTCAC CAACTAGCTG      660

GTGTCTCCCT CGACCCCAGC TGTAAG                                          686

(2) INFORMATION FOR SEQ ID NO:7:

    (i) SEQUENCE CHARACTERISTICS:
        (A) LENGTH: 762 base pairs
        (B) TYPE: nucleic acid
        (C) STRANDEDNESS: single
        (D) TOPOLOGY: linear

    (ii) MOLECULE TYPE: DNA (genomic)

    (ix) FEATURE:
        (A) NAME/KEY: intron
        (B) LOCATION: 1..108

    (ix) FEATURE:
        (A) NAME/KEY: exon
        (B) LOCATION: 109..295

    (ix) FEATURE:
        (A) NAME/KEY: intron
        (B) LOCATION: 296..459

    (ix) FEATURE:
        (A) NAME/KEY: exon
        (B) LOCATION: 460..663

    (ix) FEATURE:
        (A) NAME/KEY: intron
        (B) LOCATION: 664..762

    (xi) SEQUENCE DESCRIPTION: SEQ ID NO:7:

AGTGTCATAG ATCAGAGAAG GAGGAGATAG CCAATTCCAC CTGAGAGGAA GGGGGCTCAG       60

GGAAACTGGA GGTACGAAGA ACCTGCTAAC CTGCTGGCTC TCCCCCAGAC CCCATGCTGC      120

ACTATGTGGG CTTCGTCCCT GTCATTGATG GAGACTTCAT CCCCGCTGAC CCGATCAACC      180

TGTACGCCAA CGCCGCCGAC ATCGACTATA TAGCAGGCAC CAACAACATG GACGGCCACA      240

TCTTCGCCAG CATCGACATG CCTGCCATCA ACAAGGGCAA CAAGAAAGTC ACGGAGTAGC      300

GGGGGCACAG GACTCGGGGC GTACCGTGGG GAGGGCCCGC CGGGAAAAGC ACTGGCCTGG      360

GGCCAGCCTG GCGGAGGAAG GCAATTGAGT CAGGACTGGG AGTCGAAGTT AGCACGGTCG      420

GGTGAGTATG TGTCAGTGCC CTTACCTTGA ATTCCCCAGG GAGGACTTCT ACAAGCTGGT      480

CAGTGAGTTC ACAATCACCA AGGGGCTCAG AGGCGCCAAG ACGACCTTTG ATGTCTACAC      540

CGAGTCCTGG GCCCAGGACC CATCCCAGGA GAATAAGAAG AAGACTGTGG TGGACTTTGA      600

GACCGATGTC CTCTTCCTGG TGCCCACCGA GATTGCCCTA GCCCAGCACA GAGCCAATGC      660

CAAGTGAGGA TCTTGGCAGC GGGTGGCTCC TTGGGTCGGC TCCTTGGGGT TCCTGGGTTC      720

GCATTCCAGC CGAGTCTCGC TGTGGGTGGC TCTAGGTGTG GG                        762

(2) INFORMATION FOR SEQ ID NO:8:

    (i) SEQUENCE CHARACTERISTICS:
        (A) LENGTH: 358 base pairs
        (B) TYPE: nucleic acid
```

-continued (C) STRANDEDNESS: single
(D) TOPOLOGY: linear (ii) MOLECULE TYPE: DNA (genomic)

(ix) FEATURE:
(A) NAME/KEY: intron
(B) LOCATION: 1..111

(ix) FEATURE:
(A) NAME/KEY: exon
(B) LOCATION: 112..308

(ix) FEATURE:
(A) NAME/KEY: intron
(B) LOCATION: 309..358

(xi) SEQUENCE DESCRIPTION: SEQ ID NO:8:

```
ACTCTCTTCA TGTGATCCAC ACTCCCCCCC TGACCGATCC TCACATCAGT CGTCTCTGGC     60

TGATCGGTCC CAGTGAGACC CTGCCTGCCT ACTTGGGTGG TCTCTCCCCA GGAGTGCCAA    120

GACCTACGCC TACCTTTTTC CCATCCCTCT CGGATGCCCG TCTACCCCAA ATGGGTGGGG    180

GCCGACCATG CAGATGACAT TCAGTACGTT TTCGGGAAGC CCTTCGCCAC CCCCACGGGC    240

TACCGGCCCC AAGACAGGAC AGTCTCTAAG GCCATGATCG CCTACTGGAC CAACTTTGCC    300

AAAACAGGGT AAGACGCTGG GCCTTGGAGT GCAGGCTGAG GGCAACAGCC GAGAAGGC      358
```

(2) INFORMATION FOR SEQ ID NO:9:

(i) SEQUENCE CHARACTERISTICS:
(A) LENGTH: 617 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: intron
(B) LOCATION: 1..147

(ix) FEATURE:
(A) NAME/KEY: exon
(B) LOCATION: 148..500

(ix) FEATURE:
(A) NAME/KEY: intron
(B) LOCATION: 501..617

(xi) SEQUENCE DESCRIPTION: SEQ ID NO:9:

```
CACAGCCCGA TGCCCAGTAT GCATGGAGGG TATGGTCCCA GGGCTACTAG CTCAGAGGGG     60

TGGGGATGGC TCAGGCGTGC AGGTGCAGTA GCAGGCTTCA GCCTCCTGGG AGTCCCCGCC    120

CCTGCACAGC CTCTTCTCAC TCTGCAGGGA CCCCAACATG GGCGACTCGG CTGTGCCCAC    180

ACACTGGGAA CCCTACACTA CGGAAAACAG CGGCTACCTG GAGATCACCA AGAAGATGGG    240

CAGCAGCTCC ATGAAGCGGA GCCTGAGAAC CAACTTCCTG CGCTACTGGA CCCTCACCTA    300

TCTGGCGCTG CCCACAGTGA CCGACCAGGA GGCCACCCCT GTGCCCCCCA CAGGGGACTC    360

CGAGGCCACT CCCGTGCCCC CCACGGGTGA CTCCGAGACC GCCCCCGTGC CGCCCACGGG    420

TGACTCCGGG GCCCCCCCCG TGCCGCCCAC GGGTGACTCC GGGGCCCCCC CCGTGCCGCC    480

CACGGGTGAC TCCGGGGCCC GTACCCCACC TTGGGTGACA CTGAGGCTGA CCCCATCCCC    540

GCTACGGTGA CTCTGAGGCT GCCCCCGTGC CCCCCTCAGG TGATCTCGAG GCTCCCGCGT    600

ACCCCTACGG TGACTCT                                                   617
```

-continued (2) INFORMATION FOR SEQ ID NO:10:

(i) SEQUENCE CHARACTERISTICS:
(A) LENGTH: 344 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: intron
(B) LOCATION: 1..15

(ix) FEATURE:
(A) NAME/KEY: exon
(B) LOCATION: 16..336

(ix) FEATURE:
(A) NAME/KEY: intron
(B) LOCATION: 337..344

(xi) SEQUENCE DESCRIPTION: SEQ ID NO:10:

```
CCCTCTCATC TGGAGCCCCC GTGCCGCCCA CGGGTGACTC CGGGGCCCCC CCCGTGCCGC     60

CCACGGGTGA CTCCGGGGCC CCCCCCGTGC CGCCCACGGG TGACTCCGGG GCCCCCCCCG    120

TGCCGCCCAC GGGTGACTCC GGCGCCCCCC CCGTGCCGCC CACGGGTGAC GCCGGGCCCC    180

CCCCCGTGCC GCCCACGGGT GACTCCGGCG CCCCCCCCGT GCCGCCCACG GGTGACTCCG    240

GGGCCCCCCC CGTGACCCCC ACGGGTGACT CCGAGACCGC CCCCGTGCCG CCCACGGGTG    300

ACTCCGGGGC CCCCCCTGTG CCCCCCACGG GTGACTGTGC ATCG                     344
```

(2) INFORMATION FOR SEQ ID NO:11:

(i) SEQUENCE CHARACTERISTICS:
(A) LENGTH: 354 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: intron
(B) LOCATION: 1..65

(ix) FEATURE:
(A) NAME/KEY: exon
(B) LOCATION: 66..232

(ix) FEATURE:
(A) NAME/KEY: intron
(B) LOCATION: 233..304

(ix) FEATURE:
(A) NAME/KEY: exon
(B) LOCATION: 305..334

(xi) SEQUENCE DESCRIPTION: SEQ ID NO:11:

```
CCGGTGACTC TGAGGCCCGT GCCCGTGCCC ACCTTGGGTG AGACACTGAG GCTGCCCCAT     60

CCCAGCTGAG GCTGCCCCTG TGCCCCCCAC AGATGACTCC AAGGAAGCTC AGATGCCTGC    120

AGTCATTAGG TTTTAGCGTC CCATGAGCCT TGGTATCAAG AGGCCACAAG AGTGGGACCC    180

CAGGGGCTCC CCTCCCATCT TGAGCTCTTC CTGAATAAAG CCTCATACCC CTGTCCTGGC    240

GTCTTTCTTT GCTCTCAAGG GCTAGCTGAC GGGGAGTGGA CCTCAGTTAC CCTTACAGCA    300

CCAGGGGGCC CAACTGTACC CATCACCTGG TACAAAAAAA AAAAAAAAGA ATTC          354
```

(2) INFORMATION FOR SEQ ID NO:12:

-continued

```
     (i) SEQUENCE CHARACTERISTICS:
          (A) LENGTH: 2487 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 104..2341

    (xi) SEQUENCE DESCRIPTION: SEQ ID NO:12:

GAATTCCGGA TCAATACAGT TTACCTTCTG TATCAGTTAA GTGTCAAGAT GGAAGGAACA      60

GCAGTCTCAA GATAATGCAA AGAGTTTATT CATCCAGAGG CTG ATG CTC ACC ATG       115
                                                Met Leu Thr Met
                                                  1

GGG CGC CTG CAA CTG GTT GTG TTG GGC CTC ACC TGC TGC TGG GCA GTG       163
Gly Arg Leu Gln Leu Val Val Leu Gly Leu Thr Cys Cys Trp Ala Val
  5                  10                  15                  20

GCG AGT GCC GCG AAG CTG GGC GCC GTG TAC ACA GAA GGT GGG TTC GTG       211
Ala Ser Ala Ala Lys Leu Gly Ala Val Tyr Thr Glu Gly Gly Phe Val
                 25                  30                  35

GAA GGC GTC AAT AAG AAG CTC GGC CTC CTG GGT GAC TCT GTG GAC ATC       259
Glu Gly Val Asn Lys Lys Leu Gly Leu Leu Gly Asp Ser Val Asp Ile
             40                  45                  50

TTC AAG GGC ATC CCC TTC GCA GCT CCC ACC AAG GCC CTG GAA AAT CCT       307
Phe Lys Gly Ile Pro Phe Ala Ala Pro Thr Lys Ala Leu Glu Asn Pro
         55                  60                  65

CAG CCA CAT CCT GGC TGG CAA GGG ACC CTG AAG GCC AAG AAC TTC AAG       355
Gln Pro His Pro Gly Trp Gln Gly Thr Leu Lys Ala Lys Asn Phe Lys
     70                  75                  80

AAG AGA TGC CTG CAG GCC ACC ATC ACC CAG GAC AGC ACC TAC GGG GAT       403
Lys Arg Cys Leu Gln Ala Thr Ile Thr Gln Asp Ser Thr Tyr Gly Asp
 85                  90                  95                 100

GAA GAC TGC CTG TAC CTC AAC ATT TGG GTG CCC CAG GGC AGG AAG CAA       451
Glu Asp Cys Leu Tyr Leu Asn Ile Trp Val Pro Gln Gly Arg Lys Gln
                105                 110                 115

GTC TCC CGG GAC CTG CCC GTT ATG ATC TGG ATC TAT GGA GGC GCC TTC       499
Val Ser Arg Asp Leu Pro Val Met Ile Trp Ile Tyr Gly Gly Ala Phe
            120                 125                 130

CTC ATG GGG TCC GGC CAT GGG GCC AAC TTC CTC AAC AAC TAC CTG TAT       547
Leu Met Gly Ser Gly His Gly Ala Asn Phe Leu Asn Asn Tyr Leu Tyr
        135                 140                 145

GAC GGC GAG GAG ATC GCC ACA CGC GGA AAC GTC ATC GTG GTC ACC TTC       595
Asp Gly Glu Glu Ile Ala Thr Arg Gly Asn Val Ile Val Val Thr Phe
    150                 155                 160

AAC TAC CGT GTC GGC CCC CTT GGG TTC CTC AGC ACT GGG GAC GCC AAT       643
Asn Tyr Arg Val Gly Pro Leu Gly Phe Leu Ser Thr Gly Asp Ala Asn
165                 170                 175                 180

CTG CCA GGT AAC TAT GGC CTT CGG GAT CAG CAC ATG GCC ATT GCT TGG       691
Leu Pro Gly Asn Tyr Gly Leu Arg Asp Gln His Met Ala Ile Ala Trp
                185                 190                 195

GTG AAG AGG AAT ATC GCG GCC TTC GGG GGG GAC CCC AAC AAC ATC ACG       739
Val Lys Arg Asn Ile Ala Ala Phe Gly Gly Asp Pro Asn Asn Ile Thr
            200                 205                 210

CTC TTC GGG GAG TCT GCT GGA GGT GCC AGC GTC TCT CTG CAG ACC CTC       787
Leu Phe Gly Glu Ser Ala Gly Gly Ala Ser Val Ser Leu Gln Thr Leu
        215                 220                 225

TCC CCC TAC AAC AAG GGC CTC ATC CGG CGA GCC ATC AGC CAG AGC GGC       835
Ser Pro Tyr Asn Lys Gly Leu Ile Arg Arg Ala Ile Ser Gln Ser Gly
```

-continued

```
    230                 235                 240

GTG GCC CTG AGT CCC TGG GTC ATC CAG AAA AAC CCA CTC TTC TGG GCC      883
Val Ala Leu Ser Pro Trp Val Ile Gln Lys Asn Pro Leu Phe Trp Ala
245                 250                 255                 260

AAA AAG GTG GCT GAG AAG GTG GGT TGC CCT GTG GGT GAT GCC GCC AGG      931
Lys Lys Val Ala Glu Lys Val Gly Cys Pro Val Gly Asp Ala Ala Arg
                265                 270                 275

ATG GCC CAG TGT CTG AAG GTT ACT GAT CCC CGA GCC CTG ACG CTG GCC      979
Met Ala Gln Cys Leu Lys Val Thr Asp Pro Arg Ala Leu Thr Leu Ala
            280                 285                 290

TAT AAG GTG CCG CTG GCA GGC CTG GAG TAC CCC ATG CTG CAC TAT GTG     1027
Tyr Lys Val Pro Leu Ala Gly Leu Glu Tyr Pro Met Leu His Tyr Val
        295                 300                 305

GGC TTC GTC CCT GTC ATT GAT GGA GAC TTC ATC CCC GCT GAC CCG ATC     1075
Gly Phe Val Pro Val Ile Asp Gly Asp Phe Ile Pro Ala Asp Pro Ile
    310                 315                 320

AAC CTG TAC GCC AAC GCC GCC GAC ATC GAC TAT ATA GCA GGC ACC AAC     1123
Asn Leu Tyr Ala Asn Ala Ala Asp Ile Asp Tyr Ile Ala Gly Thr Asn
325                 330                 335                 340

AAC ATG GAC GGC CAC ATC TTC GCC AGC ATC GAC ATG CCT GCC ATC AAC     1171
Asn Met Asp Gly His Ile Phe Ala Ser Ile Asp Met Pro Ala Ile Asn
                345                 350                 355

AAG GGC AAC AAG AAA GTC ACG GAG GAG GAC TTC TAC AAG CTG GTC AGT     1219
Lys Gly Asn Lys Lys Val Thr Glu Glu Asp Phe Tyr Lys Leu Val Ser
            360                 365                 370

GAG TTC ACA ATC ACC AAG GGG CTC AGA GGC GCC AAG ACG ACC TTT GAT     1267
Glu Phe Thr Ile Thr Lys Gly Leu Arg Gly Ala Lys Thr Thr Phe Asp
        375                 380                 385

GTC TAC ACC GAG TCC TGG GCC CAG GAC CCA TCC CAG GAG AAT AAG AAG     1315
Val Tyr Thr Glu Ser Trp Ala Gln Asp Pro Ser Gln Glu Asn Lys Lys
    390                 395                 400

AAG ACT GTG GTG GAC TTT GAG ACC GAT GTC CTC TTC CTG GTG CCC ACC     1363
Lys Thr Val Val Asp Phe Glu Thr Asp Val Leu Phe Leu Val Pro Thr
405                 410                 415                 420

GAG ATT GCC CTA GCC CAG CAC AGA GCC AAT GCC AAG AGT GCC AAG ACC     1411
Glu Ile Ala Leu Ala Gln His Arg Ala Asn Ala Lys Ser Ala Lys Thr
                425                 430                 435

TAC GCC TAC CTG TTT TCC CAT CCC TCT CGG ATG CCC GTC TAC CCC AAA     1459
Tyr Ala Tyr Leu Phe Ser His Pro Ser Arg Met Pro Val Tyr Pro Lys
            440                 445                 450

TGG GTG GGG GCC GAC CAT GCA GAT GAC ATT CAG TAC GTT TTC GGG AAG     1507
Trp Val Gly Ala Asp His Ala Asp Asp Ile Gln Tyr Val Phe Gly Lys
        455                 460                 465

CCC TTC GCC ACC CCC ACG GGC TAC CGG CCC CAA GAC AGG ACA GTC TCT     1555
Pro Phe Ala Thr Pro Thr Gly Tyr Arg Pro Gln Asp Arg Thr Val Ser
    470                 475                 480

AAG GCC ATG ATC GCC TAC TGG ACC AAC TTT GCC AAA ACA GGG GAC CCC     1603
Lys Ala Met Ile Ala Tyr Trp Thr Asn Phe Ala Lys Thr Gly Asp Pro
485                 490                 495                 500

AAC ATG GGC GAC TCG GCT GTG CCC ACA CAC TGG GAA CCC TAC ACT ACG     1651
Asn Met Gly Asp Ser Ala Val Pro Thr His Trp Glu Pro Tyr Thr Thr
                505                 510                 515

GAA AAC AGC GGC TAC CTG GAG ATC ACC AAG AAG ATG GGC AGC AGC TCC     1699
Glu Asn Ser Gly Tyr Leu Glu Ile Thr Lys Lys Met Gly Ser Ser Ser
            520                 525                 530

ATG AAG CGG AGC CTG AGA ACC AAC TTC CTG CGC TAC TGG ACC CTC ACC     1747
Met Lys Arg Ser Leu Arg Thr Asn Phe Leu Arg Tyr Trp Thr Leu Thr
        535                 540                 545

TAT CTG GCG CTG CCC ACA GTG ACC GAC CAG GAG GCC ACC CCT GTG CCC     1795
```

-continued

```
Tyr Leu Ala Leu Pro Thr Val Thr Asp Gln Glu Ala Thr Pro Val Pro
    550                 555                 560

CCC ACA GGG GAC TCC GAG GCC ACT CCC GTG CCC CCC ACG GGT GAC TCC     1843
Pro Thr Gly Asp Ser Glu Ala Thr Pro Val Pro Pro Thr Gly Asp Ser
565                 570                 575                 580

GAG ACC GCC CCC GTG CCG CCC ACG GGT GAC TCC GGG GCC CCC CCC GTG     1891
Glu Thr Ala Pro Val Pro Pro Thr Gly Asp Ser Gly Ala Pro Pro Val
                585                 590                 595

CCG CCC ACG GGT GAC TCC GGG GCC CCC CCC GTG CCG CCC ACG GGT GAC     1939
Pro Pro Thr Gly Asp Ser Gly Ala Pro Pro Val Pro Pro Thr Gly Asp
            600                 605                 610

TCC GGG GCC CCC CCC GTG CCG CCC ACG GGT GAC TCC GGG GCC CCC CCC     1987
Ser Gly Ala Pro Pro Val Pro Pro Thr Gly Asp Ser Gly Ala Pro Pro
        615                 620                 625

GTG CCG CCC ACG GGT GAC TCC GGG GCC CCC CCC GTG CCG CCC ACG GGT     2035
Val Pro Pro Thr Gly Asp Ser Gly Ala Pro Pro Val Pro Pro Thr Gly
    630                 635                 640

GAC TCC GGG GCC CCC CCC GTG CCG CCC ACG GGT GAC TCC GGC GCC CCC     2083
Asp Ser Gly Ala Pro Pro Val Pro Pro Thr Gly Asp Ser Gly Ala Pro
645                 650                 655                 660

CCC GTG CCG CCC ACG GGT GAC GCC GGG CCC CCC CCC GTG CCG CCC ACG     2131
Pro Val Pro Pro Thr Gly Asp Ala Gly Pro Pro Pro Val Pro Pro Thr
                665                 670                 675

GGT GAC TCC GGC GCC CCC CCC GTG CCG CCC ACG GGT GAC TCC GGG GCC     2179
Gly Asp Ser Gly Ala Pro Pro Val Pro Pro Thr Gly Asp Ser Gly Ala
            680                 685                 690

CCC CCC GTG ACC CCC ACG GGT GAC TCC GAG ACC GCC CCC GTG CCG CCC     2227
Pro Pro Val Thr Pro Thr Gly Asp Ser Glu Thr Ala Pro Val Pro Pro
        695                 700                 705

ACG GGT GAC TCC GGG GCC CCC CCT GTG CCC CCC ACG GGT GAC TCT GAG     2275
Thr Gly Asp Ser Gly Ala Pro Pro Val Pro Pro Thr Gly Asp Ser Glu
    710                 715                 720

GCT GCC CCT GTG CCC CCC ACA GAT GAC TCC AAG GAA GCT CAG ATG CCT     2323
Ala Ala Pro Val Pro Pro Thr Asp Asp Ser Lys Glu Ala Gln Met Pro
725                 730                 735                 740

GCA GTC ATT AGG TTT TAGCGTCCCA TGAGCCTTGG TATCAAGAGG CCACAAGAGT     2378
Ala Val Ile Arg Phe
                745

GGGACCCCAG GGGCTCCCCT CCCATCTTGA GCTCTTCCTG AATAAAGCCT CATACCCCTG   2438

GGGCCCAACT GTACCCATCA CCTGGTACAA AAAAAAAAAA AAAGAATTC               2487
```

(2) INFORMATION FOR SEQ ID NO:13:

(i) SEQUENCE CHARACTERISTICS:
(A) LENGTH: 745 amino acids
(B) TYPE: amino acid
(D) TOPOLOGY: linear (ii) MOLECULE TYPE: protein (xi) SEQUENCE DESCRIPTION: SEQ ID NO:13:

```
Met Leu Thr Met Gly Arg Leu Gln Leu Val Val Leu Gly Leu Thr Cys
  1               5                  10                  15

Cys Trp Ala Val Ala Ser Ala Ala Lys Leu Gly Ala Val Tyr Thr Glu
             20                  25                  30

Gly Gly Phe Val Glu Gly Val Asn Lys Lys Leu Gly Leu Leu Gly Asp
         35                  40                  45

Ser Val Asp Ile Phe Lys Gly Ile Pro Phe Ala Ala Pro Thr Lys Ala
     50                  55                  60
```

-continued

```
Leu Glu Asn Pro Gln Pro His Pro Gly Trp Gln Gly Thr Leu Lys Ala
 65                  70                  75                  80

Lys Asn Phe Lys Lys Arg Cys Leu Gln Ala Thr Ile Thr Gln Asp Ser
                 85                  90                  95

Thr Tyr Gly Asp Glu Asp Cys Leu Tyr Leu Asn Ile Trp Val Pro Gln
            100                 105                 110

Gly Arg Lys Gln Val Ser Arg Asp Leu Pro Val Met Ile Trp Ile Tyr
        115                 120                 125

Gly Gly Ala Phe Leu Met Gly Ser Gly His Gly Ala Asn Phe Leu Asn
    130                 135                 140

Asn Tyr Leu Tyr Asp Gly Glu Glu Ile Ala Thr Arg Gly Asn Val Ile
145                 150                 155                 160

Val Val Thr Phe Asn Tyr Arg Val Gly Pro Leu Gly Phe Leu Ser Thr
                165                 170                 175

Gly Asp Ala Asn Leu Pro Gly Asn Tyr Gly Leu Arg Asp Gln His Met
            180                 185                 190

Ala Ile Ala Trp Val Lys Arg Asn Ile Ala Ala Phe Gly Gly Asp Pro
        195                 200                 205

Asn Asn Ile Thr Leu Phe Gly Glu Ser Ala Gly Gly Ala Ser Val Ser
    210                 215                 220

Leu Gln Thr Leu Ser Pro Tyr Asn Lys Gly Leu Ile Arg Arg Ala Ile
225                 230                 235                 240

Ser Gln Ser Gly Val Ala Leu Ser Pro Trp Val Ile Gln Lys Asn Pro
                245                 250                 255

Leu Phe Trp Ala Lys Lys Val Ala Glu Lys Val Gly Cys Pro Val Gly
            260                 265                 270

Asp Ala Ala Arg Met Ala Gln Cys Leu Lys Val Thr Asp Pro Arg Ala
        275                 280                 285

Leu Thr Leu Ala Tyr Lys Val Pro Leu Ala Gly Leu Glu Tyr Pro Met
    290                 295                 300

Leu His Tyr Val Gly Phe Val Pro Val Ile Asp Gly Asp Phe Ile Pro
305                 310                 315                 320

Ala Asp Pro Ile Asn Leu Tyr Ala Asn Ala Ala Asp Ile Asp Tyr Ile
                325                 330                 335

Ala Gly Thr Asn Asn Met Asp Gly His Ile Phe Ala Ser Ile Asp Met
            340                 345                 350

Pro Ala Ile Asn Lys Gly Asn Lys Lys Val Thr Glu Glu Asp Phe Tyr
        355                 360                 365

Lys Leu Val Ser Glu Phe Thr Ile Thr Lys Gly Leu Arg Gly Ala Lys
    370                 375                 380

Thr Thr Phe Asp Val Tyr Thr Glu Ser Trp Ala Gln Asp Pro Ser Gln
385                 390                 395                 400

Glu Asn Lys Lys Lys Thr Val Val Asp Phe Glu Thr Asp Val Leu Phe
                405                 410                 415

Leu Val Pro Thr Glu Ile Ala Leu Ala Gln His Arg Ala Asn Ala Lys
            420                 425                 430

Ser Ala Lys Thr Tyr Ala Tyr Leu Phe Ser His Pro Ser Arg Met Pro
        435                 440                 445

Val Tyr Pro Lys Trp Val Gly Ala Asp His Ala Asp Asp Ile Gln Tyr
    450                 455                 460

Val Phe Gly Lys Pro Phe Ala Thr Pro Thr Gly Tyr Arg Pro Gln Asp
465                 470                 475                 480

Arg Thr Val Ser Lys Ala Met Ile Ala Tyr Trp Thr Asn Phe Ala Lys
```

-continued

```
                485                 490                 495

Thr Gly Asp Pro Asn Met Gly Asp Ser Ala Val Pro Thr His Trp Glu
            500                 505                 510

Pro Tyr Thr Thr Glu Asn Ser Gly Tyr Leu Glu Ile Thr Lys Lys Met
        515                 520                 525

Gly Ser Ser Ser Met Lys Arg Ser Leu Arg Thr Asn Phe Leu Arg Tyr
    530                 535                 540

Trp Thr Leu Thr Tyr Leu Ala Leu Pro Thr Val Thr Asp Gln Glu Ala
545                 550                 555                 560

Thr Pro Val Pro Pro Thr Gly Asp Ser Glu Ala Thr Pro Val Pro Pro
                565                 570                 575

Thr Gly Asp Ser Glu Thr Ala Pro Val Pro Pro Thr Gly Asp Ser Gly
            580                 585                 590

Ala Pro Pro Val Pro Pro Thr Gly Asp Ser Gly Ala Pro Pro Val Pro
        595                 600                 605

Pro Thr Gly Asp Ser Gly Ala Pro Pro Val Pro Pro Thr Gly Asp Ser
    610                 615                 620

Gly Ala Pro Pro Val Pro Pro Thr Gly Asp Ser Gly Ala Pro Pro Val
625                 630                 635                 640

Pro Pro Thr Gly Asp Ser Gly Ala Pro Pro Val Pro Pro Thr Gly Asp
                645                 650                 655

Ser Gly Ala Pro Pro Val Pro Pro Thr Gly Asp Ala Gly Pro Pro Pro
            660                 665                 670

Val Pro Pro Thr Gly Asp Ser Gly Ala Pro Pro Val Pro Pro Thr Gly
        675                 680                 685

Asp Ser Gly Ala Pro Pro Val Thr Pro Thr Gly Asp Ser Glu Thr Ala
    690                 695                 700

Pro Val Pro Pro Thr Gly Asp Ser Gly Ala Pro Pro Val Pro Pro Thr
705                 710                 715                 720

Gly Asp Ser Glu Ala Ala Pro Val Pro Pro Thr Asp Asp Ser Lys Glu
                725                 730                 735

Ala Gln Met Pro Ala Val Ile Arg Phe
            740                 745
```